US008641655B2

(12) United States Patent
Rambod et al.

(10) Patent No.: US 8,641,655 B2
(45) Date of Patent: *Feb. 4, 2014

(54) ENHANCED CLEARANCE IN AN ARTIFICIAL KIDNEY INCORPORATING A PULSATILE PUMP

(75) Inventors: Edmond Rambod, Los Angeles, CA (US); Victor Gura, Beverly Hills, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 475 days.

This patent is subject to a terminal disclaimer.

(21) Appl. No.: 12/977,931

(22) Filed: Dec. 23, 2010

(65) Prior Publication Data

US 2011/0125073 A1    May 26, 2011

Related U.S. Application Data

(60) Division of application No. 11/942,626, filed on Nov. 19, 2007, now Pat. No. 7,871,390, which is a continuation-in-part of application No. 10/940,862, filed on Sep. 14, 2004, now Pat. No. 7,309,323, which is a continuation-in-part of application No. 10/085,349, filed on Nov. 16, 2001, now Pat. No. 6,960,179.

(60) Provisional application No. 60/866,357, filed on Nov. 17, 2006.

(51) Int. Cl.
*A61M 37/00* (2006.01)
*C02F 1/44* (2006.01)

(52) U.S. Cl.
USPC .......... 604/5.04; 210/645; 210/646; 210/739; 604/6.09; 604/6.11

(58) Field of Classification Search
USPC .......... 604/6.09, 6.11, 5.01, 5.04, 6.15, 6.16; 210/645–646, 600, 634, 644, 195.2, 210/416.1, 433.1, 321.71, 500.21, 258, 259, 210/739; 422/44
See application file for complete search history.

(56) References Cited

U.S. PATENT DOCUMENTS 4,269,708 A    5/1981  Bonomini et al.
4,861,485 A *  8/1989  Fecondini ..................... 210/641
(Continued)

OTHER PUBLICATIONS

Office Action, U.S. Appl. No. 11/933,533 mailed on Jun. 3, 2010.
(Continued)

*Primary Examiner* — Leslie Deak
(74) *Attorney, Agent, or Firm* — Hamilton, Brook, Smith & Reynolds, P.C.

(57) ABSTRACT

A continuous renal replacement therapy (CRRT) device is provided that weighs between 2 and 10 pounds. The CRRT device can be portable, mobile or completely worn on the person of the patient. Blood and dialysate are each pumped in a pulsed or pulsatile manner through a dialyzer such that a significant portion of the peak pulse of the blood flow coincides with a significant portion of a low pulse portion of the dialysate flow. An differential pressure between a dialysate inlet of the dialyzer and the blood inlet of the dialyzer periodically changes from a high differential pressure of between 70 and 120 mmHg for a first time period and a low differential pressure of between −10 and 10 mmHg for a first time period and a low differential pressure of between −10 and 10 mmHg for a second time period. The frequency of the high and low differential pressure cycle is between about 0.5 and 4 Hz.

15 Claims, 14 Drawing Sheets

(56) References Cited

U.S. PATENT DOCUMENTS

| | | | |
|---|---|---|---|
| 5,902,336 | A | 5/1999 | Mishkin |
| 5,910,252 | A | 6/1999 | Truitt et al. |
| 6,685,664 | B2 | 2/2004 | Levin et al. |
| 6,706,007 | B2 | 3/2004 | Gelfand et al. |
| 6,758,975 | B2 | 7/2004 | Peabody et al. |
| 6,776,912 | B2 | 8/2004 | Baurmeister |
| 6,796,955 | B2 | 9/2004 | O'Mahoney et al. |
| 6,843,779 | B1 | 1/2005 | Andrysiak et al. |
| 6,890,315 | B1 | 5/2005 | Levin et al. |
| 7,033,498 | B2 | 4/2006 | Wong |
| 7,309,323 | B2 | 12/2007 | Gura |
| 7,351,218 | B2 | 4/2008 | Bene |
| 7,597,677 | B2 | 10/2009 | Gura et al. |
| 7,828,761 | B2 | 11/2010 | Gura et al. |
| 7,871,390 | B2 * | 1/2011 | Rambod et al. .............. 604/5.04 |
| 7,896,829 | B2 | 3/2011 | Gura et al. |
| 7,896,830 | B2 | 3/2011 | Gura et al. |
| 8,137,299 | B2 | 3/2012 | Gura et al. |
| 8,206,331 | B2 | 6/2012 | Gura et al. |
| 2002/0112609 | A1 | 8/2002 | Wong |
| 2003/0236482 | A1 | 12/2003 | Gorsuch et al. |
| 2006/0241543 | A1 | 10/2006 | Gura |

OTHER PUBLICATIONS

Office Action, U.S. Appl. No. 12/574,128 mailed on Aug. 4, 2011.

Ronco, Claudio, et al., "The Vicenza Wearable Artifical Kidney for Peritoneal Dialysis (ViWAK PD)," Blood Purification, 2007, pp. 383-388.

Rozga, Jacek, et al., "A Novel Plasma Filtration Therapy for Hepatic Failure: Preclinical Studies," Therapeutic Apheresis and Dialysis, 2006, pp. 138-144, Blackwell Publishing Asia Pty. Ltd.

Runge, T.M., et al., "Hemodialysis: Evidence of Enchanted Molecular Clearance and Ultrafiltration Volume By Using Pulsatile Flow," The International Journal of Artificial Organs, vol. 16, 1993, pp. 645-652.

Sanchez, Cesar, et al., Continuous Venovenous Renal Replacement Therapy Using a Conventional Infusion Pump, ASAIO Journal, 2001, pp. 321-324.

Shettigar, "Portable Artificial Kidney with Advantages of Hemodialysis, Hemofiltration, and Hemoperfusion," Artifical Organs, 1982, vol. 1981, No. 5; pp. 645-649.

Shettigar, et al., "A portable hemodialysis/hemofiltration system independent of dialysate and infusion fluid." Artif Organs, vol. 7, No. 2, May 1983, pp. 254-256.

Shinzato, Tom, et al., "Newly Developed Economical and Efficient Push/Pull Hemodiafiltration," Effective Hemodiafiltration: New Methods, Contib Nephrol, 1994, pp. 79-86, vol. 108.

Siaghy, E.M., et al., "Consequences of Static and Pulsatile on Transmembrane Exchanges During Vitro Microdialysis: Implication for Studies in Cardiac Physiology," Med Biol Eng Comput, vol. 37, 1999, pp. 196-201.

Suri, R., et al., "Adequacy of Quotidian Hemodialysis," American Journal of Kidney Disease, vol. 42 Suppl. 1, 2003, pp. S42-S48.

Tsuruta, Kazuma, et al., "A Simple Method for Clinical Application of Push/Pull Hemodiafiltration," Effective Hemodiafiltration: New Methods, 1994, pp. 71-78, Contrib Nephrol, vol. 108.

Utsunomiya, T., et al., "Effect of Direct Pulsatile Peritoneal Dialysis on Peritoneal Permeability and Lymphatic Absorption in the Rat," Nippon Jinzo Gakkai Shi, vol. 37, 1995, pp. 24-28.

Vermeulen, Ph.D., Theodore, et al., "Adsorption and Ion Exchange," Perry's Chemical Engineers' Handbook, 1973, Fifth Edition, Section 16, pp. 16-1 to 16-16.

Welty, J.R., et al., "Chapter 27: Unsteady-state Molecular Diffusion," Fundamentals of Momentum, Heat, and Mass Transfer ($2^{nd}$ ed.), McGraw-Hill, New York, 1984.

United States Patent and Trademark Office, Non-Final Office Action, U.S. Appl. No. 12/636,501, Mailing Date: Nov. 15, 2011.

* cited by examiner

| | ROLLER PUMP | PULSATILE PUMP |
|---|---|---|
| $Q_{B.in}$ (ml/min) | 52 | 50 |
| $Q_{D.in}$ (ml/min) | 34 | 38 |
| UF (ml/min) | 6.3 | 16.8 |
| $P_{B.out}$ (mmHg) | 27 | 20 |
| $P_{D.out}$ (mmHg) | 2 | -32 |
| TMP (mmHg) | 23 | 51 |

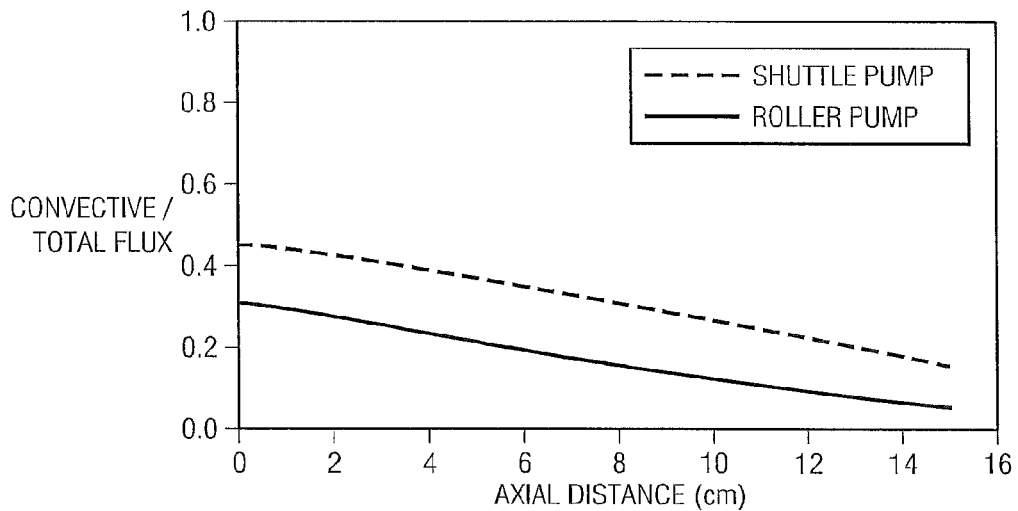

FIG. 10

| ROLLER PUMP | | | | UREA CLEARANCE | | | | | |
|---|---|---|---|---|---|---|---|---|---|
| | | | | EXPERIMENTAL | | NUMERICAL | | ERROR (%) | |
| $Q_{B,in}$ (ml/min) | $Q_{D,in}$ (ml/min) | TMP (mmHg) | UF (ml/min) | Mod. | Std. | Mod. | Std. | Mod. | Std. |
| 82 | 50 | 48 | 9.7 | 37 | 31 | 40 | 34 | -7 | -10 |
| 65 | 40 | 21 | 7.0 | 31 | 27 | 34 | 30 | -9 | -11 |
| 52 | 34 | 23 | 6.3 | 30 | 27 | 30 | 27 | 0* | 0* |
| 42 | 20 | 21 | 6.3 | 24 | 21 | 24 | 20 | 2 | 2 |
| 23 | 9 | 22 | 3.9 | 13 | 11 | 12 | 10 | 5 | 7 |

* DIFFUSION PERMEABILITY WAS DETERMINED FROM THIS EXPERIMENTAL CASE

| PULSATILE PUMP | | | | UREA CLEARANCE | | | | | |
|---|---|---|---|---|---|---|---|---|---|
| | | | | EXPERIMENTAL | | NUMERICAL | | ERROR (%) | |
| $Q_{B,in}$ (ml/min) | $Q_{D,in}$ (ml/min) | TMP (mmHg) | UF (ml/min) | Mod. | Std. | Mod. | Std. | Mod. | Std. |
| 77 | 42 | 66 | 24.4 | 44 | 28 | 48 | 33 | -7 | -17 |
| 50 | 38 | 51 | 16.8 | 43 | 39 | 37 | 31 | 14 | 22 |
| 43 | 36 | 47 | 14.2 | 40 | 39 | 34 | 29 | 17 | 26 |

RELATIVELY HIGH %ERROR FOR THE SHUTTLE PUMP IS DUE TO THE NON-LINEAR RELATIONSHIP BETWEEN HYDRAULIC PERMEABILITY AND TMP

FIG. 11

| ROLLER PUMP | | | | CREATININE CLEARANCE | | | | | |
|---|---|---|---|---|---|---|---|---|---|
| | | | | EXPERIMENTAL | | NUMERICAL | | ERROR (%) | |
| $Q_{B,in}$ (ml/min) | $Q_{D,in}$ (ml/min) | TMP (mmHg) | UF (ml/min) | Mod. | Std. | Mod. | Std. | Mod. | Std. |
| 82 | 50 | 48 | 9.7 | 34 | 27 | 37 | 31 | -8 | -12 |
| 65 | 40 | 21 | 7.0 | 30 | 26 | 32 | 28 | -5 | -7 |
| 52 | 34 | 23 | 6.3 | 28 | 25 | 28 | 25 | 0* | 0* |
| 42 | 20 | 21 | 6.3 | 23 | 20 | 23 | 19 | 2 | 3 |
| 23 | 9 | 22 | 3.9 | 13 | 11 | 12 | 10 | 4 | 5 |

* DIFFUSION PERMEABILITY WAS DETERMINED FROM THIS EXPERIMENTAL CASE

| WAK PUMP | | | | CREATININE CLEARANCE | | | | | |
|---|---|---|---|---|---|---|---|---|---|
| | | | | EXPERIMENTAL | | NUMERICAL | | ERROR (%) | |
| $Q_{B,in}$ (ml/min) | $Q_{D,in}$ (ml/min) | TMP (mmHg) | UF (ml/min) | Mod. | Std. | Mod. | Std. | Mod. | Std. |
| 77 | 42 | 66 | 24.4 | 40 | 21 | 45 | 29 | -12 | -34 |
| 50 | 38 | 51 | 16.8 | 40 | 34 | 35 | 27 | 12 | 21 |
| 43 | 36 | 47 | 14.2 | 40 | 39 | 32 | 26 | 21 | 33 |

*FIG. 12*

| ROLLER PUMP | | | | POTASSIUM CLEARANCE | | | | | |
|---|---|---|---|---|---|---|---|---|---|
| | | | | EXPERIMENTAL | | NUMERICAL | | ERROR (%) | |
| $Q_{B,in}$ (ml/min) | $Q_{D,in}$ (ml/min) | TMP (mmHg) | UF (ml/min) | Mod. | Std. | Mod. | Std. | Mod. | Std. |
| 82 | 50 | 48 | 9.7 | 43 | 37 | 43 | 38 | -2 | -3 |
| 65 | 40 | 21 | 7.0 | 37 | 33 | 37 | 33 | 0* | 0* |
| 52 | 34 | 23 | 6.3 | 34 | 32 | 32 | 30 | 6 | 7 |
| 42 | 20 | 21 | 6.3 | 26 | 23 | 24 | 21 | 6 | 7 |
| 23 | 9 | 22 | 3.9 | 14 | 12 | 12 | 10 | 12 | 16 |

* DIFFUSION PERMEABILITY WAS DETERMINED FROM THIS EXPERIMENTAL CASE

| WAK PUMP | | | | POTASSIUM CLEARANCE | | | | | |
|---|---|---|---|---|---|---|---|---|---|
| | | | | EXPERIMENTAL | | NUMERICAL | | ERROR (%) | |
| $Q_{B,in}$ (ml/min) | $Q_{D,in}$ (ml/min) | TMP (mmHg) | UF (ml/min) | Mod. | Std. | Mod. | Std. | Mod. | Std. |
| 77 | 42 | 66 | 24.4 | 46 | 31 | 50 | 37 | -10 | -22 |
| 50 | 38 | 51 | 16.8 | 41 | 37 | 39 | 34 | 5 | 9 |
| 43 | 36 | 47 | 14.2 | 41 | 40 | 35 | 32 | 13 | 20 |

ENHANCED CLEARANCE IN AN ARTIFICIAL KIDNEY INCORPORATING A PULSATILE PUMP

CROSS-REFERENCE TO RELATED APPLICATIONS

This is a divisional of U.S. application Ser. No. 11/942,626, filed Nov. 19, 2007 now U.S. Pat No. 7,871,390, which is a continuation-in-part of U.S. patent application Ser. No. 10/940,862, filed Sep. 14, 2004, entitled WEARABLE CONTINUOUS RENAL REPLACEMENT THERAPY DEVICE, which issued as U.S. Pat. No. 7,309,323 on Dec. 18, 2007, which is a continuation-in-part of U.S. patent application Ser. No. 10/085,349, filed Nov. 16, 2001, entitled WEARABLE CONTINUOUS RENAL REPLACEMENT THERAPY DEVICE, which issued as U.S. Pat. No. 6,960,179 on Nov. 1, 2005, all of which are hereby incorporated by reference. This application further claims priority from pending U.S. Provisional Application No. 60/866,357 filed Nov. 17, 2006, entitled ENHANCED CLEARANCE IN AN ARTIFICIAL KIDNEY INCORPORATING A PULSATILE PUMP, which is also incorporated herein by reference.

TECHNICAL FIELD

The present invention is directed to dialysis systems, and more particularly to dialysis systems that may be completely and continuously worn by a patient or dialysis systems that are portable or mobile.

BACKGROUND

Hemodialysis is a process by which microscopic toxins are removed from the blood using a filtering membrane such as a dialyzer. Typically, hemodialysis is administered to a patient in periodic three to four hour sessions. Each session takes place two or three times per week. There exists a growing body of research that prefers daily dialysis since increased dialysis time improves outcomes, both in terms of quality of life and patient longevity. An additional number of researchers believe that continuous dialysis for twenty-four hours a day, seven days a week would provide the best outcome for a patient in terms of quality of life and longevity. The actual implementation of substantially continuous dialysis has been impossible to date because of technology and cost constraints. Regardless, it is believed that continuous renal replacement therapy (CRRT) would be an enormous improvement over intermittent dialysis because far more toxins can be removed from the blood using a CRRT device seven days a week and for nearly twenty-four hours a day.

Some advantages of providing CRRT include an expected decrease in morbidity and mortality, a decrease in the amount of medications required, a decrease in fluid intake, a decrease of dietary restrictions, and numerous improvements to the quality of life of the end-stage renal disease (ESRD) patients. Present day CRRT machines are stationary, large, heavy machines adapted to provide dialysis, hemofiltration or a combination of both to individual patients. The existing CRRT are cumbersome and require electrical, connection to 120-140 volt AC electrical outlets as well as several feet of tubing to connect the machine to the patient. In addition, these machines require a continuous supply of gallons of fresh filtered water to create the dialysate fluid. Furthermore, a patient must remain connected to the existing heavy and cumbersome CRRT machine for many hours each day, which limits his or her ability to perform normal, everyday activities.

An additional problem with existing dialysis machines is that frequent reconnection and disconnection to the machine requires accessing blood flow in a patient by puncturing an artiovenous shunt. These shunts only last for limited periods of time and subject the patient to infection, clotting and other complications which result in numerous hospitalizations and repeated surgical interventions. Another problem with existing dialysis machines is as these machines become smaller and a bit more portable, smaller hemofilters or dialyzer filters must be used that does not clog or clot too quickly so that extended or continuous dialysis can be performed. A common type of dialyzer includes nine hundred or more cylindrical hollow fibers through which blood flow is provided. The hundreds of cylindrical hollow fibers are contained in a shell or container in which dialysate fluid is circulated around and past the exterior walls of the hollow fibers. The exterior walls of the hollow fibers or lumens are semi-porous so that impurities in the blood can be moved from the blood and into the dialysate. One problem that occurs in a dialyzer is the clogging or clotting of blood flow within individual hollow fibers. Such clogging of blood flow through the fibers decreases the effectiveness of the dialyzer's filtration and blood cleaning properties. Furthermore, it is understood that proteins and other compounds or substances in the blood may clog the pores of the semi-porous membrane overtime and decrease the effectiveness of the dialyzer filter. If a dialyzer filter is to be in continuous operation twenty-four hours a day, seven days a week, it is important that such a dialyzer be operational for extended periods of time at or near a continued peak performance without becoming clogged or having its efficiency decreased significantly during usage. Furthermore, it would also be useful if a dialyzer remained efficient and effective when a low-power pump is used to pump blood there through such that a minimum amount of energy is required for the highest possible clearance of impurities from a patient's blood at the lowest amount of required energy.

Dialyzers' membranes have been studied for well over a half of a century. The initial inventors of dialysis or dialactic therapy understand the basics of diffusion and how toxins diffuse across a dialyzer's membrane from blood to a dialysate fluid. There are many factors that influence diffusion in solute transfer across a semi-permeable membrane. Such factors have been explained in various prior articles about the workings of a dialyzer. But, again there has been limited or minimal research on providing a dialysis device wherein the dialyzer operates efficiently over extended periods of time (more than 15 hours) in order to provide a low power completely wearable or portable dialysis device having a dialyzer with increased efficiency over that of previous dialysis machines having a dialyzer with a membrane of the same or similar membrane surface area.

SUMMARY

Embodiments of the invention provide a continuous renal replacement therapy (CRRT) device that weighs between 2 and 10 pounds. The CRRT device can be portable, mobile or completely worn on the person of the patient. Blood and dialysate are each pumped in a pulsed or pulsatile manner through a dialyzer such that a significant portion of the peak pulse of the blood flow and pressure coincides with a significant portion of a low pulse flow and pressure portion of the dialysate flow. A differential pressure between a dialysate inlet of the dialyzer and the blood inlet of the dialyzer periodically changes from a high differential pressure of between 70 and 120 mmHg for a first time period and a low differential pressure of between −10 and 10 mmHg for a second time period. The frequency of the high and low differential pressure cycle is between about 0.5 and 4 Hz.

In one aspect thereof an exemplary embodiment of the invention provides a continuous renal replacement therapy (CRRT) device. The CRRT device includes a blood pump channel that establishes a pulsed or pulsatile blood flow. The pulsed blood flow is periodic such that each period of the blood flow comprises a high blood pressure portion having a first duration and a low blood pressure portion having a second duration. The first duration and the second duration have a duration ratio between about 3:4 and 4:3. The duration ratio requires that the time durations of the high blood pressure portion and low blood pressure portions are at least 75 percent (%) of each other. For example, if the high blood pressure portion of the pulse has a duration of one (1) second, then the low blood pressure pulse should have a duration of between about 0.75 and 1.25 seconds. The exemplary embodiment further comprises a dialysate pump channel that provides a pulsed or pulsatile dialysate flow. The pulsed dialysate flow is periodic such that each period comprises a high dialysate pressure portion having said second duration and a low dialysate pressure portion having said first duration. The high blood pressure portion and said low dialysate pressure portion occur, at least in part, during a same first periodic time frame. The exemplary embodiment also comprises a dialyzer or hemofilter. The dialyzer comprises a blood inlet that receives the pulsed blood flow from the blood pump channel. The dialyzer of the exemplary embodiment also comprises a plurality of fibers. Each fiber comprises a semi permeable membrane exterior and a lumen extending the length of the fiber. The lumen provides a passage through the fiber for the pulsed blood flow to flow. The dialyzer further comprises a blood outlet for the pulsed blood flow to exit said dialyzer as well as a dialysate inlet for receiving the pulsed dialysate flow being pumped by the dialysate pump channel. Also the dialyzer has an outer tube that establishes a dialysate container or chamber, about the plurality of fibers. In other words, the fibers are substantially contained in the dialyzer and are within a dialysate chamber or container. The pulsed dialysate flow flows through the dialysate chamber. The semi permeable membranes of the plurality of fibers are the means between each said lumen and said dialysate chamber. The dialyzer includes a dialysate outlet for the pulsed dialysate flow to exit the dialyzer. The combination of the blood pump channel, the dialysate channel and the dialyzer are configured to establish a peak Trans Membrane Pressure (TMP) across the semi permeable membranes of the plurality of fibers and between said pulsed blood flow in the lumens and the pulsed dialysate flow in the dialysate chamber. The peak TMP occurs during the first periodic time frame. The peak TMP is between about 70 mmHg and 120 mmHg.

Various embodiments of an exemplary CRRT device require that the low blood pressure portion of the blood flow and the high dialysate pressure portion of the dialysate flow both occur, at least in part, during a second periodic time frame. Furthermore, the blood channel, the dialysate channel and said dialyzer are configured to establish a minimum TMP across the semi permeable membranes of the plurality of fibers during said second periodic time frame. The minimum TMP is between about 10 mmHg and −10 mmHg.

Additionally in various embodiments on an exemplary CRRT device a dual channel ventricle pulsatile pump that comprises the blood pump channel and the dialysate pump channel is incorporated into the device. The same mechanical mechanism may be utilized in the dual channel ventricle pulsatile pump to actuate both the blood pump channel and the dialysate channel.

Furthermore, some embodiments of the invention may be entirely worn on the person of the user, while other embodiments of the CRRT device are light weight (e.g., between 2 and 15 pounds while operating) and mobile such that they may be moved about a medical facility or within a user's home.

Some embodiments of an exemplary CRRT device provide blood pump channel that may provide a pulsed or pulsatile blood flow with a periodic flow rate of between 0.5 and 4 Hz and wherein the dialysate pump channel provides a pulsed or pulsatile dialysate flow with a same or similar periodic flow rate. This periodic flow rate of blood has been found to be the least damaging to the blood cells as they pass through the blood pump channel and also deter clogging or clotting of the blood in the pump channel, the fiber lumens in the dialyzer, as well as in the semi permeable membranes between the fiber lumens and dialysate within the dialysate chamber portion of the dialyzer. The pulsed or pulsatile blood flow described herein appears to provide an unexpected washing or push-pull effect that helps to inhibit clogging for the extended operating time periods of exemplary CRRT devices. It should be noted that exemplary CRRT devices' elements combine in an unexpected manner such that the peak TMP that occurs during the first periodic time frame and the minimum TMP that occurs during the second periodic time frame inhibit clogging of the lumens and the semi permeable membranes.

In another exemplary embodiment a continuous renal replacement therapy (CRRT) device is provided that comprises a blood pump channel for providing a pulsatile blood flow. The pulsatile blood flow is periodic such that each period comprises a high blood pressure portion having a first time duration and a low blood pressure portion having a second time duration. The first time duration and the second time duration have a duration ratio of between about 3:4 and about 4:3, this, of course, includes a duration ratio of 1:1. These exemplary embodiments further include a dialysate pump channel that provides a pulsatile dialysate flow. The pulsatile dialysate flow is a periodic flow such that each period of the flow comprises a high dialysate pressure portion having the second time duration and a low dialysate pressure portion having the first time duration; wherein said high blood pressure portion and said low dialysate pressure portion occur periodically, at least in part, during a same first periodic time frame. The exemplary embodiment further includes a dialyzer. The dialyzer comprises a blood inlet for receiving the pulsatile blood flow. The dialyzer also comprises a plurality of fibers wherein each fiber comprises a lumen extending the length of the fiber and a semi permeable membrane exterior. The lumen is for carrying the pulsatile blood flow through a substantial portion of the dialyzer. The dialyzer further includes a blood outlet for said pulsatile blood flow to exit the dialyzer, a dialysate inlet for receiving the pulsatile dialysate flow, a dialysate compartment area that is around or about the plurality of fibers, for said pulsatile dialysate flow to flow through; and a dialysate outlet for the pulsatile dialysate flow to exit said dialyzer. The combination of the blood pump channel, the dialysate channel and the dialyzer are configured to establish a peak blood inlet-to-dialysate outlet differential pressure that occurs during the first periodic time frame. The peak blood inlet-to-dialysate outlet differential pressure may be in a range of between about 60 mmHg and about 150 mmHg, which provides an unexpected enhanced amount of toxins from a patient's blood to move across the fiber semi permeable membrane into dialysate contained within and pulsing through the dialyzer.

Additional embodiments of an exemplary CRRT device are configured such that the low blood pressure portion and the high dialysate pressure portion both occur, at least in part, during a second periodic time frame. The blood pump channel, the dialysate channel and the dialyzer are configured to establish a minimum blood inlet-to-dialysate outlet differential pressure that occurs during the second periodic time frame and that establishes a differential pressure between about 10 mmHg and about −10 mmHg.

Other embodiments of the invention provide a method of continuous renal replacement therapy (CRRT). An exemplary method of providing CRRT comprises pumping blood, by a pulsatile blood pump, to provide a pulsatile blood flow. The pulsatile blood flow is a periodic flow wherein each period comprises a high blood pressure portion having a first time duration and a low blood pressure portion having a second time duration. The first time duration and the second time duration have a duration ratio that can range between about 3:4 and 4:3. The method of providing CRRT further includes pumping dialysate, by a pulsatile dialysate pump, to provide a pulsatile dialysate flow. The pulsatile dialysate flow, like the pulsatile blood flow, has a period that comprises a high dialysate pressure portion having the second time duration and a low dialysate pressure portion having the first time duration. The high blood pressure portion and the low dialysate portion occur, at least in part, during a first periodic time frame. The exemplary method further establishes a blood inlet-to-dialysate outlet differential pressure between a blood inlet of a dialyzer and a dialysate outlet of the dialyzer; wherein said blood inlet to-dialysate outlet differential pressure oscillates between a maximum differential pressure and a minimum differential pressure at a pump frequency of between 0.5 and 4 Hz. The maximum differential pressure has a range of between about 60 mmHg and about 150 mmHg. The minimum differential pressure has a range of between about 10 mmHg and about −10 mmHg for the pump frequency of between 0.5 and 4 Hz.

All though two separate pulsatile pumps could be used in an exemplary method of CRRT, is various embodiments the pulsatile blood pump and said pulsatile dialysate pump are each a separate pump channel of a dual channel pulsatile pump and are each operated by a same mechanical mechanism. Embodiments of the invention utilize a pulsatile blood pump and a pulsatile dialysate pump that provides an average pulsatile flow rate of between 30 and 90 milliliters/minute (ml/min).

In yet another embodiment of the invention a method of dialysis is provided that comprises receiving blood in a blood circuit of a dialysis device; pumping the blood in a pulsed manner to provide an average pulsatile blood flow rate of between 30 and 90 ml/min; pumping dialysate, in a dialysate circuit of the dialysis device, in a pulsed manner to provide an average pulsatile dialysate flow rate of between 30 and 90 ml/min; receiving the pumped blood at a blood inlet of a dialyzer; receiving the pumped dialysate at a dialysate inlet of said dialyzer, to establish a pressure differential between the blood in said blood inlet and the dialysate in the dialysate inlet that fluctuates at a periodic rate of between 0 mmHg+/−10 mmHg and 120 mmHg+/−20 mmHg; transferring urea molecules from the blood to the dialysate while the blood and the dialysate are passing through the dialyzer; and cleaning said dialysate by a filtration means so that the cleaned dialysate can be reused and recirculated in the dialysate circuit.

Embodiments of the invention provide a method to CRRT that can be performed by either a completely wearable or a completely portable dialysis device.

Various embodiments of the invention provide one or more pumping devices that pump the blood and the dialysate such that a peak flow of said blood occurs at alternating times with a peak flow of the dialysate. And, various embodiments of the invention are configured such that the pumping o, f the blood in a pulsed manner comprises providing, in an alternating manner, a high blood flow rate portion and a low blood flow rate portion, and wherein said pumping dialysate in a pulsed manner comprises providing, in an alternating manner, a high dialysate flow rate portion and a low dialysate flow rate portion. The high blood flow rate portion and the low dialysate flow rate portion each occurring, at least for a majority of their durations, at the same time.

As such, various embodiments of exemplary methods and devices for CRRT have been found to operate to provide enhance clearances in an artificial kidney when a pulsed or pulsatile pump is used in combination with other elements discussed herein to produce an unexpected solution to a problem faced by renal failure patients, but that has never been effectively solved to provide a completely wearable or portable CRRT device that is operable to enhance the quality of life of such patients and to unexpectedly resist clogging or clotting of blood in its dialyzer element.

BRIEF DESCRIPTION OF THE DRAWINGS

For a more complete understanding, reference is now made to the following description taken in conjunction with the accompanying Drawings in which:

FIG. 10 provides a graph illustrating experimentally calculated and estimated ratios of convective urea flux across a semi permeable membrane in a roller pump configuration and in an exemplary shuttle or pulsatile pump configuration;

FIG. 11 provides a chart that provides experimental and numerical results for urea clearance with a roller pump and an exemplary pulsed pump design for various blood and dialysate fluid flow rates;

FIG. 12 provides a chart that provides experimental and numerical results for creatinine clearance with a roller pump and an exemplary pulsed pump design for various blood and dialysate fluid flow rates;

DETAILED DESCRIPTION

Figure 1:
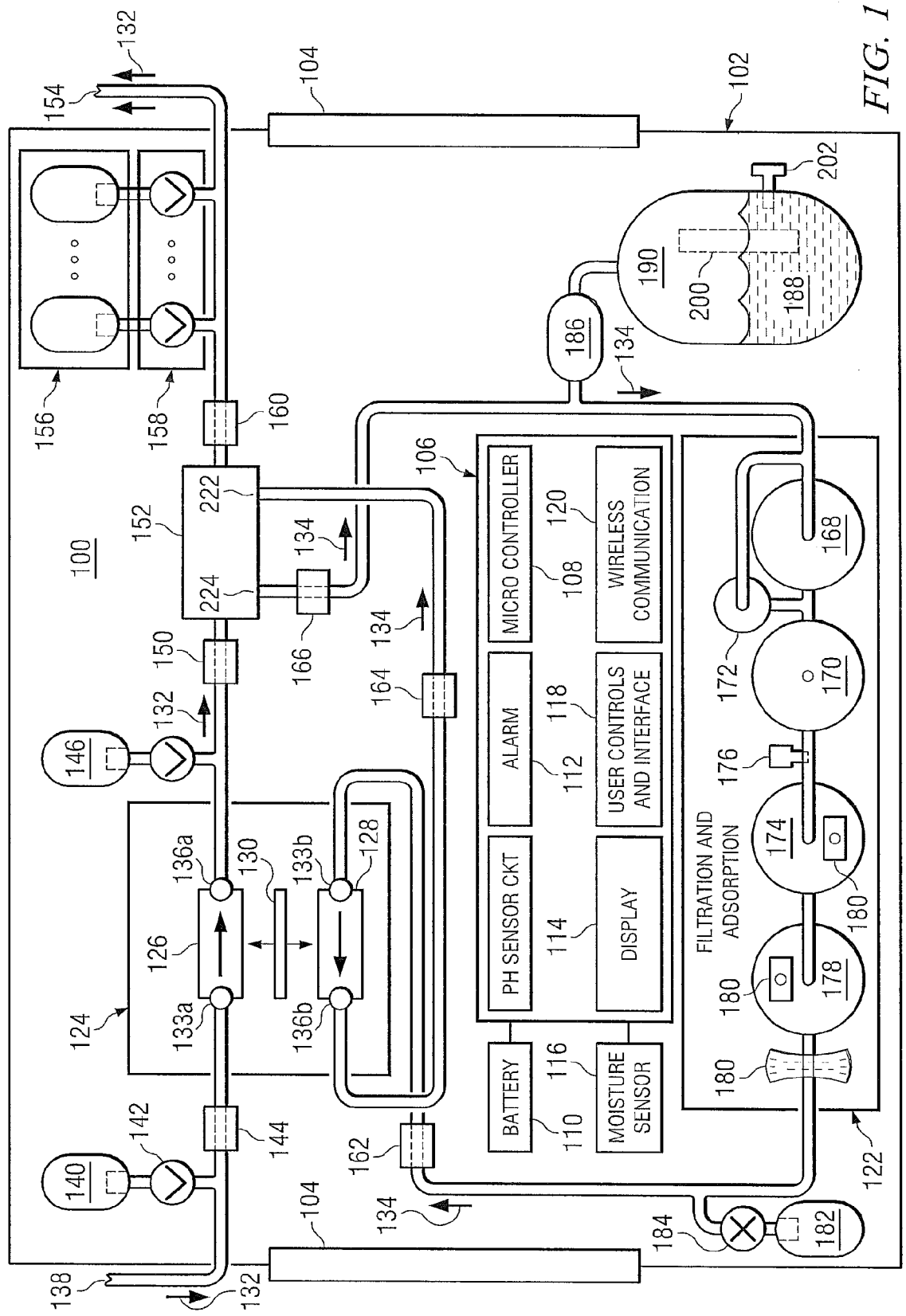
FIG. 1 illustrates an exemplary portable or completely wearable dialysis device diagram in accordance with an embodiment of the invention.

Referring now to the drawings, wherein like reference numbers are used herein to designate like elements throughout, the various views and embodiments of the exemplary enhanced clearance artificial kidneys incorporating a pulsatile pump are illustrated and described, and other possible embodiments are described. The figures are not necessarily drawn to scale, and in some instances the drawings have been exaggerated and/or simplified in places for illustrative purposes only. One of ordinary skill in the art will appreciate the many possible applications and variations based on the following examples of possible embodiments.

An exemplary embodiment of a wearable CRRT device is depicted in FIG. 1. Wearable CRRT device 100 is built into, or is part of a patient wearable strap, belt or other wearable apparatus 102. The belt or strap 102 may include a pair of end portions 104 that are adapted to be secured together by a fastening means (not specifically shown). The end portion/fastening means 104 could be any number of fastening devices suitable to secure the ends of the waist belt or shoulder strap together over the shoulder of the patient. Such fastening means is not limited to snaps, buttons, buckles, clips, laces, hook and loops, zippers, harnesses, clasps, etc. One embodiment of an exemplary CRRT device 100 may be envisioned to be in the shape of an ammunition or military supply belt. It could also be in the shape of a waist or fanny pack. Other embodiments may be in the shape of a small backpack. An exemplary wearable CRRT device 100 is to be worn continuously by a patient either over or under the patient's clothing. Other embodiments are portable devices substantially contained in a carry bag, brief case, purse, or backpack style container.

One or more circuit cards or microcircuits 106 are incorporated within the wearable CRRT device 100. A microcontroller 108 is utilized to control and monitor various aspects of the wearable CRRT device 100. Microcontroller 108 is preferably a low or very low power microcontroller, but may be substantially any microcontroller adapted to operate in an exemplary CRRT device 100. One of the many functions of the microcontroller 108 is to monitor the battery 110. An exemplary CRRT device 100 will operate continuously for at least five hours to about thirty hours using, on average, less than 10 continuous watts of power. Some embodiments of the wearable CRRT device 100 will use, on average, less than 3 continuous watts of power. Embodiments of the invention will weigh between two and ten pounds when operating.

The battery 110 is removably installed in the wearable CRRT device 100. The battery 110 may be rechargeable and may be recharged either while contained in the wearable CRRT device 100 or while disconnected and removed from the wearable CRRT device 100. The battery 110 can store enough energy to power an exemplary wearable CRRT device 100 for at least five hours and in some embodiments up to thirty or more hours of continuous uninterrupted device operation. The microcontroller 106, by itself, or via additional circuitry, monitors the charge status of the battery 110. If the microcontroller 106 determines that the battery 110 is low on charge or has less than an estimated, predetermined amount of operating time left (e.g., one hour left), the microcontroller 106 may trigger an alarm condition via the alarm circuit 112. Alarm circuit 112 may provide any combination of an audio, visual or physical alarm. The physical alarm signal may include vibrations or small tingle-style shocks to the patient. An alarm condition or warning may be displayed on a display 114, which can be seen by the user. The display 114 may be a liquid crystal display, light-emitting diode display or any other low power display technology. An alarm condition may also shut down all or predetermined parts of the exemplary wearable CRRT device 100. For example, a battery low condition may slow the pump, discussed herein below, to a very low volume of blood movement through the dialyzer in order to save energy and decrease a possibility of blood clotting. The pump may be slowed to one tenth to one half of its normal pumping rate in order to conserve energy until a battery recharge or new battery is provided.

A moisture sensor 116 is in electrical communication with the microcontroller 108. The moisture sensor 116 detects high humidity, condensation, or liquid present inside the packaging or covering over (not specifically shown) the wearable CRRT device 100. In some embodiments a plurality of moisture sensors are positioned at strategic locations within the CRRT device 100. For example, the moisture sensor 116 may be positioned near the pump (to be discussed later) or the filtration and absorption section. In other embodiments, an additional moisture sensor may also be located near the dialyzer input and/or outputs.

The packaging or covering that partially or completely encloses the exemplary CRRT device 100 may be the combination of plastic, cloth, a rubberized material, a poly product, or another suitable material. The covering may cover a portion of the wearable CRRT device 100 and allow access to various parts of the device, such as the display 114 and/or the user or doctor controls 118.

High humidity, condensation or the presence of liquid inside an exemplary wearable CRRT device 100 may be indicative of patient blood leakage, dialysate leakage or other fluid leakage inside the CRRT device 100. Upon sensing moisture, the moisture sensor 116 provides a signal to the microcontroller 108 and an alarm is triggered via the alarm circuit 112. Depending on the location of the moisture sensor within the wearable CRRT device 100, different responses to sensed moisture may occur. For example, if a moisture sensor senses moisture near the blood circuit (to be described below) the CRRT device 100 may turn the pump completely off, providing audible alarm to the patient wearer and utilize the wireless communications circuitry 120 to call an emergency number for help. Conversely, if moisture is sensed near the filtration and pad absorption portion 122 of the wearable CRRT device 100, then in some embodiments the alarm circuit 112 may sound an audible or patient-sensed alarm, slow the pumping rate of the blood and dialysate and make further checks via a gas or pressure sensor for possible air contamination or bubbles within the dialysate loop of the CRRT device 100. It is noted that the wireless communication circuitry 120 may also be able to provide the geographic location of the exemplary wearable CRRT device 100 in via a wireless communication 120 to a third party who may provide help or a service to the patient.

The pump 124 is an electric pulsatile pump. Embodiments of the present invention may have a single channel pulsatile pump or a dual pulsatile pump. FIG. 1 discloses a dual channel pulsatile pump 124. Each channel of the dual channel pulsatile pump includes a rubberized tubular portion 126 and 128. Each rubberized tubular portion comprises valves at either end for directing a fluid flow through the rubberized tubular portion in a main direction (depicted by an arrow on the tubular portion 126 and 128). A motor and transmission (not specifically shown) within the pulsatile pump provides a pushing member that oscillates back and forth between the rubberized tubular portions 126 and 128 thereby alternately pressing against the resilient rubberized tubular portions and creating a pulsed flow into and out of each of the established created chambers within the rubberized tubular portions 126 and 128. There are various types of pulsatile pumps. Some such pumps use pneumatic pressure to cause the flexure of the valved chambers of the pump. In some embodiments a pulsatile electromagnetic pump may be used in order to minimize moving parts of the pump. Exemplary dual channel pulsatile pumps would use the same motor and transmission to ultimately pump in a pulsed manner both channels of the pump. This saves energy and minimizes the size of the pumping system within an exemplary wearable CRRT device 100. The microcontroller 108 can be used to control various pumping variables. Potential adjustable pumping variables include, but are not limited to, adjusting the pump stroke, the volume per stroke, the speed or number of strokes per minute of each chamber, the torque of the pump motor and transmission combination, the pumping rate (i.e., number of pump cycles per minute), the pump pressure, the pump pressure differential between the input and the output of the pump, and pump pause and cycle times. In some embodiments, the pushing member 130 may be adjusted to press against each of the flexible tubing portions 126 and 128 with longer or shorter strokes such that the volume of fluid pumped through one of the channels is larger than the volume of fluid being pumped with each pulse of the other channel of the pump. The pushing member 130 is part of a mechanical mechanism that can pump both channels (blood and dialysate) of an exemplary CRRT device.

An exemplary wearable CRRT device 100 has two fluid circuits: a blood circuit as indicated by the arrows 132 and a dialysate circuit as indicated by the arrows 134. The dual channel pulsatile pump 124 is used in the exemplary embodiment. The pulsatile pump may have rubberized flexible cartridges 126 and 128 that provide flow in a single direction or in opposing directions. The pulsatile pump 124 shown provides flow across the pump or through the pump in opposing directions. Each cartridge or pump chamber 126 has an input valve at an input side 134 of the chamber and an output valve at the output side 136 of the chamber. The input and output valves are ball values that minimize damage to the blood cells in the blood circuit. Flapper valves may also be used in various embodiments.

In the blood circuit 132 of an exemplary CRRT device 100, blood from a patient enters the blood circuit at the blood input 138 the blood flows through the blood circuit 132 where anticoagulant fluid (e.g., heparin and other reasonable equivalents) may be mixed with the blood via an anticoagulant reservoir 140 and an anticoagulant micropump 142. The anticoagulant micropump may be a piezo or diaphragm MRRO pump or other type of low energy pump for providing small amounts of anticoagulant fluid to the blood flow.

The blood flows past a first pressure sensor 144 prior to entering the input valve 134a of the dual channel pulsatile pump. When the pushing member 130 presses against the flexible rubberized tubular cartridge portion 126, the input valve 134a closes and the exit valve 136a opens and allows a pulse of blood to exit the first pulsatile chamber [126]. Additional fluid reservoirs 146 and micropumps 148 may add additional substances to the blood flow, such as anticoagulant fluids or medications. The blood then passes past a second pressure sensor 150 which senses the pressure of the output stroke of the first channel of the pulsatile pump prior to the blood entering the dialyzer 152. An exemplary blood channel pulsatile pump chamber can provide a blood flow rate of between about 15 to 100 ml per minute (pulsatile). An exemplary pulsatile pump 124 may have dimensions of 9.7×7.1×4.6 centimeters with a weight of less than 400 grams when not operating. An exemplary pump uses less than 10 watts of energy to pump two channels of fluids using a single motor, transmission and pushing member that alternately pumps each channel in a pulsatile fashion at or around 180 degrees out of phase. If the pushing means of an exemplary pulsatile pump has difficulty compressing or requires very little energy compressing one of the flexible rubberized tubular chamber portions, the pulsatile pump may provide an alarm to the microcontroller 106 indicating a possible occlusion in the blood or dialysate circuits input or output valves of a pulsatile pump channel. A low power pulsatile pump using from two to about 7 watts, steady state, may also be used successfully in exemplary embodiments of the invention.

The pulsatile pump can be tuned by adjusting the motor transmission or re-orienting the pushing member a small distance from being centered between the tubular portions 126, 128 such that the pulses or cycles of the two pulse chambers are in phase, 180 degrees out of phase, or alternating such that each chamber pumps at a predetermined number of degrees out of phase in order to utilize the pulses of the pump to aid in maximizing the dialysis process occurring in the dialyzer 152. Embodiments of exemplary pulsatile pumps may be slowed such that the blood flow or fluid flow through a chamber of the pump is between 1 and 50 ml per minute during an alarm state in the wearable CRRT device 100.

Other types of pumps can also be successfully used or incorporated into embodiments of the CRRT device 100. For example, two separate pulsatile pumps may be used provided that the pumps can be timed such that the pumps continuously pulse at predetermined alternating output rates. This can be performed with stepper motors and microprocessor control Other pumps that can provide a pulsed output such as a double-sided piston pump that has an intake stroke through one valve and a pump stroke through a second valve may also be used. Such a pump may be magnetic or pneumatically powered.

Still discussing the blood circuit 132, the blood passes by the second pressure sensor 150 and then through the hollow lumens or fibers of the dialyzer 152 (not specifically shown). The dialysis process takes place in the dialyzer wherein impurities in a patient's blood move via a mass transfer through the outer membranes of the porous lumens through which the blood is traveling. The impurities are deposited into the dialysate as they exit the outer surface of a lumen's outer membrane into the dialysate that is flowing through the dialyzer in the dialysate circuit 134.

The blood cleaned exits the dialyzer and travels toward the blood circuit output 154 to go back into the patient. As the blood flows from the dialyzer 152 to the blood circuit output 154, additional medicines, vitamins and other fluids may be added to the blood via reservoirs 156 and micropumps 158.

The pressure of the blood as it exits the dialyzer 152 is sensed at a third pressure sensor or transducer 160.

The microcontroller 108 may display pump status or other pump/flow related information such as pressure, flow rate, or dual channel pump phase difference on the display 114. User controls 118, being buttons, switches, slide controls, knobs, connectors, or touch-sensitive switches (not specifically shown) may be used to enable the patient, a physician, a nurse, technician or computer-based device to adjust various settings and controls on the exemplary CRRT device 100. Furthermore, the communication device 120 may be utilized to send and receive control settings via a paging or other telecom or wireless communication channels or networks for fine tuning or medical adjustment of the exemplary CRRT device. For example, adjustments to the pump 124 rate, flow rate, pump RPM, pulse rate or any of the micropump flow rates may all be monitored or controlled vial the user interface 118 and 114 or the wireless communication circuitry 120. A doctor may be able to monitor the CRRT device from a satellite location and be able to adjust CRRT settings remotely.

The dialyzer 152, is shown as a single dialyzer, but can be a single or multiple dialyzers connected in series or parallel. The dialyzer 152 may take the form of a cartridge that can be "clicked" or quick connected and disconnected into and out of the blood/dialysate circuits by a doctor, nurse or technician. The dialyzer 152 used in an exemplary CRRT device 100 may comprise from 0.2 to about 1 square meters of dialyzing surface area (e.g., semi permeable membrane) on the lumen fibers therein. During dialysis, the blood circuit 132 generally has blood flowing in a direction opposite that of the dialysate circuit flow through the dialyzer 152. Furthermore, it has been determined through experimentation that the pulsing of the pulsatile pumps out of phase aid in maximizing the dialysis process. In particular, embodiments of the invention that incorporate a out of phase pulsatile blood flow and dialysate flow through a dialyzer provide enhanced clearance with respect to the removal of toxins from the blood over similar systems that do not incorporate a pulsed or pulsatile dialysate in blood flow through dialyzer. Such results have been found with exemplary embodiments even when the dialysate and the blood flow through the dialyzer in the same direction.

The combination of the first, second and third pressure sensor/transducers 144, 150 and 160, provide differential measurements that can be analyzed by the microcontroller 108. For example, if the pressure differential across the dialyzer 152 is too high (from blood input to output), it may mean, among other things, that the dialyzer 152 has multiple clots or occlusions in the fiber lumens therein. A high pressure differential may also mean that the dialyzer is being operated at too high a blood flow. As a result, an alarm situation can be initiated by the microcontroller 108 or the blood pump 124 may be automatically adjusted by the microcontroller to operate at a higher or lower torque, pump rate or pulse volume such that the flow rate is decreased in predetermined increments in an attempt to stabilize or decrease the pressure differential so that blood cell damage is minimized. If a pressure at one of the pressure transducers 144, 150, 160, drops below a predetermined low pressure, it may be an indication that a fluid leak has occurred in the blood circuit or that air is being pulled into the blood circuit 132. The microcontroller 108 may shut down or slow predetermined parts of the wearable CRRT device 100 in response to pressure in the blood circuit being measured below a predetermined level. Furthermore, the microcontroller 108 may initiate an alarm condition in conjunction with the alarm circuit 112 and communication circuit 120.

Still referring to FIG. 1, the exemplary dialysate circuit 134 will now be discussed. A fourth pressure transducer 162 measures the dialysate pressure at the input side of the dialysate pump cartridge 128. The fourth pressure transducer or sensor 162 provides a pressure reading at the input of the dialysate pump cartridge to the microcontroller 108. The dialysate pump portion 128, like the blood pump portion 126 is preferably part of a dual pulsatile pump device 124 as described above. It is understood that the dialysate pulsatile pump portion may also be a separate pulsing pump device in varying embodiments.

Cleaned, fresh dialysate from the sorbent filters 122 flows through the dialysate circuit 134 past the fourth pressure transducer 162 and is pumped through the dialysate pump rubberized tubular portion 128. The dialysate portion of the dual pulsatile pump can pump dialysate at a flow rate ranging from near 0 to about 200 ml per minute (pulsatile). During normal pumping operations the operational flow rate of the dialysate through the dialysate pump is between about 40 to about 100 ml per minute (pulsatile).

Embodiments of the wearable CRRT device 100 are designed to operate using less than about 1 liter of dialysate. Other embodiments may function properly and only require between 300 ml and 400 ml of dialysate in the closed dialysate fluid circuit 134. In embodiments designed for young adults or children, the amount of dialysate needed for operation may be between about 100 to 300 ml of dialysate. Minimizing the amount of dialysate decreases the overall weight of an exemplary device and decreases the operating cost by minimizing the amount of medical waste produced by a dialyzer. The combination of dialysate and filters 122 allow the embodiment to circulate dialysate fluid for at least twenty-four hours before a filter requires replacement. In various embodiments filter replacement may be required at intervals between twenty-four and forty-eight hours. Furthermore, because less than a liter of dialysate is all that is needed in the closed dialysate circuit 134, sterile or ultra-pure dialysate can be economically used in exemplary embodiments of the wearable CRRT device 100. It is further understood that in embodiments that provide a portable and/or partially wearable CRRT device, the amount of dialysate in the dialysate circuit 134 may be greater than one liter. In fact, the amount of dialysate or ultra-pure dialysate in a portable or mobile or partially wearable device may range from 300 ml to about 5 or 6 liters of dialysate.

In existing large substantially stationary dialysis machines, it is common to use about 90 liters of dialysate per patient per run. Generally, due to the amount of water required to create the dialysate, filtered water, rather than ultra-pure water, is used in such large dialysis machines. Filtered water is much less expensive than ultra-pure or sterile water. Filtered water that is used in large present dialysis machines is allowed to have some bacteria in it. Bacteria are larger than the size of the pores in the membranes or fiber lumens used within an exemplary dialyzer 152. Since the bacteria are larger than the pore size in the semi-permeable membranes of the lumens within the dialyzer 152, the bacteria cannot cross the membrane and get into a patient's blood in the blood circuit 132.

Conversely, medical research has provided some results that are uncomfortable with the use of non-sterile dialysate (i.e., dialysate containing filtered water, bacteria, toxins, or microorganisms). Medical research has shown that microorganisms and bacteria within non-sterile dialysate create waste products, toxins or poisons in the dialysate. The waste products from the bacteria can cross the dialyzer porous membrane and get into the patient's blood while the actual bacteria itself cannot. Such toxins are referred to in some cases, as endotoxins. It has been shown that endotoxins that pass from dialysate through the dialyzer membrane to a patient's blood can have a negative impact on a patient's health. The endotoxins may result in making a patient sick.

Since exemplary embodiments of the wearable CRRT device 100 require less than one liter of dialysate, it is economically feasible to use ultra-pure or sterile water as the main ingredient in making the dialysate.

The dialysate exits the pulsatile dialysate pump portion 128 via the exit valve 136b in a pulsed pulsatile fashion and passes a fifth pressure transducer 164, which measures the dialysate pressure on the dialysate input side 222 of dialyzer 152. The dialysate in the dialysate circuit 154 pulses through the dialyzer 152 such that the dialysate moves in a direction opposite to the flow of the blood in the lumen membrane fibers in the dialyzer. Furthermore, fluids being relatively non-compressible, the peaks of the dialysate flow pulses alternate in time with the peaks of the blood flow peaks pulses through the blood circuit 132 in the dialyzer. In other words, the pulsed flow of the dialysate through the dialyzer alternates with the pulsed flow peaks of the blood through the dialyzer. In some embodiments of the invention, the alternating peak flows of the dialysate fluid and the blood through the dialyzer are about 180 degrees out of phase.

While the dialysate is in the dialyzer 152, waste products and toxins in the blood pass through the membranes of the lumens within the dialyzer and into the dialysate due to diffusion and further in embodiments of the present invention due additionally to convection and osmosis forces. The enhanced clearance of toxins from blood that occurs in embodiments of the invention is achieved in part by the trans membrane pressure (TMP) caused by the alternating pulsatile pumping action and pressure differential between the blood within the lumen membranes and the dialysate outside of the lumen fiber membranes.

The dialysate fluid exits the dialyzer 152 and flows through a sixth pressure sensor or transducer 166. The pressure transducer 166 sends a signal to the microcontroller 108 indicating the pressure of the dialysate exiting the dialyzer 152. The sensed pressure may help to indicate a clogged dialyzer, a dialysate leak or other emergency condition.

The dialysate circuit 134 moves the now used dialysate from the output of the dialyzer 152 past the pressure transducer 166 and toward the dialysate filter section 122. The used dialysate in this portion of the dialysate circuit 134 contains toxins, contaminants and other undesirable substances that have been removed from the blood of a patient. The filtration section 122 filters or reacts with the predetermined substances in the used dialysate in order to recycle the dialysate for continued re-circulation and use in the dialysate circuit. Some compounds or substances that are considered toxins or contaminants in the used dialysate are urea, creatinine, and ammonia, along with other various substances that are ordinarily removed by a patient's kidney.

In an exemplary embodiment a first filter 168 in the filtration section 122 contains urease. The urease is used to filter the used dialysate and further functions to break down urea that was removed from the blood in the dialyzer 152. When urease breaks down, urea, at least two unwanted byproducts are created. Generally, the two byproducts of broken-down urea are ammonium (ammonia) and carbon dioxide.

The dialysate with the ammonia and carbon dioxide exit the first filter 168. The urea is substantially removed from the dialysate, but the ammonia and carbon dioxide need to be removed from the dialysate also. The dialysate, ammonia, and carbon dioxide enter the second filter 170. The second filter 170 contains a compound zirconium or zirconium phosphate (i.e., ZrPx). The zirconium in the second filter 170 captures the ammonia. It is understood by those having ordinary skill in the art of dialysis chemistry that various chemicals and derivations thereof can be utilized to achieve the same or similar results.

The zirconium or second filter 170 will eventually become saturated with ammonia. When saturated or near saturation, the zirconium filter 170 will become less efficient at removing ammonia from the dialysate. It is not advantageous to allow ammonia or ammonium to circulate through the dialysate circuit and back to the dialyzer. Thus, in an exemplary wearable or portable CRRT device 100, a sensor 176 is placed in the dialysate circuit after the zirconium filter 170 in order to sense the presence of ammonia in the dialysate. The sensor 176 may be a pH sensor, an ammonia specific sensor, or a conductivity sensor. Various probe and electromagnetic style sensors may be used herein to sense conductivity pH or the amount of ammonia in the dialysate after flowing through the zirconium filter. If an ammonia sensor is used, it will sense whether a predetermined amount of ammonia is present in the dialysate. If a. pH sensor is used, it would sense whether the pH of the dialysate has become a predetermined amount more alkaline than an acceptable amount, i.e., the alkalinity of the dialysate is outside of an acceptable range of alkalinity. As more ammonia is present in the dialysate, the dialysate becomes more alkaline. It is noted that depending on the actual chemicals and absorbents used in the filters, the dialysate may become more acidic and as such a sensor would be used to sense the same. If a conductivity sensor is used, it would sense the conductivity changes of the dialysate. If the conductivity of the dialysate is outside of a predetermined range then it could be determined that ammonia is increasing in the dialysate. An electromagnetic sensor may also be used to sense the conductivity across the dialysate in a manner that would sense a changing conductivity (i.e., ammonia) within the dialysate.

The sensor 176 is in electrical communication with the microcontroller 108. If the signal provided by the sensor 176 to the microcontroller 108 indicates that ammonia within the dialysate exceeds a predetermined amount (i.e., the pH or conductivity are outside a predetermined range), then the microcontroller may conclude that the zirconium filter 170 is not absorbing a majority of or a predetermined percentage of the ammonia in the dialysate flow there through. As a result, an alarm condition may be triggered by the microcontroller 108. The alarm condition may instruct the user that one or more of the filter cartridges for filter sections in the filtration section 122 require replacement. The alarm condition may also decrease the pumping rate or flow rate of one or both channels of the pulsatile pump 124. Slowing the pump rate of the dual channel pulsatile pump 124 may increase the amount of ammonia absorbed by the zirconium filter 170 due to a decreased flow rate of the dialysate there through. Furthermore, the alarm condition may decrease the dialysate flow rate and increase or decrease the blood flow rate through an exemplary wearable or portable CRRT device 100 by adjusting the position or motion of the pressing means 130.

The sensor 176 that is used to sense the presence of ammonia in the dialysate should be placed after the second filter 170 containing the zirconium phosphate. In other embodiments, the sensor 176 may be placed after the third filter 174, which contains hydrous zirconium oxide or after the fourth filter 178, which contains carbon. In other embodiments of the invention, a single filter may be used containing layers or a mixture of the contents of the four filters discussed above. Furthermore, a parallel filter 172 may be placed in parallel with another filter, for example filter 168, in order to decrease the pressure drop across one or more filters in the filtration section 122. Both filters that are in parallel (i.e., 172 and 176) may each be layered filters with various filtration and adsorbent substances therein. Furthermore, the layers may be mixed, for example, carbon particles may be mixed throughout the entire filter among the layers of urease and zirconium or zirconium phosphate. Furthermore, the zirconium and zirconium phosphate may be mixed together within one or more filters. All in all, the filtration section 122 of an exemplary embodiment may comprise one or more filter cartridges or filters that react with or adsorb substances found in the used dialysate such that the dialysate will be renewed for continued circulation and usage in the dialysate circuit 134.

The third exemplary filter 174 comprises hydrous zirconium oxide, which may further remove contaminants and ammonia from the dialysate. A bubbler, degasser, valve device, or hydrophilic membrane ("degasser") 180 may be part of each of the filters or filtered portions or be a separate element there from. A degasser 180 is used in an exemplary embodiment to remove air, carbon dioxide and other gas bubbles that may form or be found in the dialysate circuit 134. It is important that a very limited amount of gas bubbles go through the dialyzer 152. As such, a degasser 180 should be positioned prior to the dialysate pump portion of the pulsatile pump 124 and after one or more of the filtration filters in the filtration section 122 with respect to the dialysate flow direction in the dialysate circuit 134.

A fourth exemplary filter 178 contains carbon and is used to further clean the dialysate of impurities via adsorption. The first, second, third and fourth filter sections 168, 170, 174, 178, may be designed as combinational or separate filter sections. Each cartridge can be inserted and removed from an exemplary wearable portable CRRT device 100 by the patient, doctor, technician, or nurse. Each filter cartridge may contain layers or combinations of chemicals or adsorbents. In fact, an exemplary embodiment may have a single cartridge filter containing layers of required substances to clean and refresh the dialysate after passing through the dialyzer 152. The cartridges may be installed in a series, a parallel or a combination of a series and parallel formation. Furthermore, the filter cartridge or cartridges may incorporate a degasser 180 thereon or such a degasser may be separate element downstream from one or more of the dialysate filters or the dialysate filter section 122.

The filter section or individual filter cartridges require replacement at intervals ranging from about twelve hours to forty-eight hours. Through experimentation, if the total volume of all of the combinations of all the sorbent materials needed, in necessary quantities, combined, will be between 400 cm$^3$ and 2,500 cm$^3$ and will not require changing or replacement for 24 to 48 hours while the embodiment is pumping dialysate at a flow rate of about 20 to 70 ml/min.

An additive reservoir 182 and micropump 184 may be connected to the dialysate circuit 134 after the filtration section 122, but before the dialysate input side 133b. Although not specifically shown in FIG. 1, multiple reservoirs 182 and micropumps 184 can be connected to the dialysate circuit 134. The micropump 184 may be any of the micropumps discussed above with respect to the micropump 142. Here, the micropump 184 and reservoir 182 may add chemicals and additives that refresh the dialysate and prolong its ability to act as a dialysate. An exemplary wearable CRRT device 100 may have as little as 300 ml to as much as about 1 liter of dialysate within the dialysate circuit 134. An exemplary portable CRRT device may have from 300 ml to about 5 liters of dialysate. It is important for the sorbent section or filtration portion 122 to be able to clean and refresh the dialysate continuously as the dialysate circulates about the dialysate circuit 134.

In various exemplary wearable or portable CRRT devices 100, ultrafiltrate or other fluids may be removed from the patient's blood in addition the dialysis process. If a patient's kidneys are not functioning properly, it may be important to remove excess fluids from the patient's blood as well as blood contaminants such as urea and creatinine. In the dialysate circuit between where the dialysate exits the dialyzer 152 and enters the filtration section 122 of various exemplary embodiments, ultrafiltrate/dialysate, along with other contaminants and fluids obtained via the dialyzer 152, can be tapped off or removed from the dialysate circuit 134. The ultrafiltrate 188 may be deposited in a bladder or reservoir 190. The bladder or reservoir 190 may be contained within or hang below an exemplary wearable or portable CRRT device 100 and be able to store from about 0.1 to perhaps 2 liters of ultrafiltrate fluid. A fullness sensor associated with the fluid bladder 190 is in electrical communication with the microcontroller 108 to enable an alarm condition or fluid fullness reading in the ultrafiltrate bladder 190 when the bladder fullness reaches a certain level or volume. The fluid bladder 190 may also be incorporated into the wearable or portable CRRT device 100 as an empty cartridge that is filled via a micropump and valve combination (not specifically shown). A fullness sensor 200 may aid the microcontroller to determine the fullness of the cartridge bladder 190 and may turn off the ultrafiltrate supplying pump and provide a signal to the user that the cartridge needs emptying. In various embodiments, the fluid bladder or cartridge 190 may contain an absorbent material (also not specifically shown) for absorbing fluid present in the bladder and to prevent sloshing. The absorbent material may be cotton, polymer, sponge, a compressed material, powder, a gel, or other material that absorbs fluid and/or limits the sloshing in the bladder or cartridge. The bladder may be designed to expand as it fills. The bladder may press against the micro switch (not specifically shown) when it is full or expanded thereby providing a fullness signal to the microprocessor 108.

In some embodiments, the ultrafiltrate cartridge or bladder 190 may incorporate a means for emptying the fluid bladder 202 thereon in the form of a cap, stopper, valve, removable inner bladder tubing or otherwise.

Exemplary embodiments of a wearable or portable CRRT device 100 can provide therapy to a patient that incorporates basic dialysis, a complex dialysis regime, ultrafiltration and various medicinal therapies to and for patient. As discussed, there continues to be a growing body of literature indicating that increasing dialysis time, which incorporates both longer and more frequent dialysis treatments, may be associated with improved outcomes and treatment of End Stage Renal Disease (ESRD) patients, both in terms of life expectancy as well as expected morbidity and mortality.

During experimentation with embodiments of the present invention, there were concerns related to continuous and consistent solute transport across the membranes of the hollow fibers within the dialyzer 152 for the extended 24 hour periods of time. Furthermore, additional concerns related to potential clotting or clogging of the individual fiber membranes in the dialyzer 152 that would limit the lifespan and usefulness of the dialyzer 152 for less than twenty-four to forty-eight hours. Different types of pumps including roller pumps, centrifuge pumps and pulsatile pumps were used as a pumping mechanism for the blood circuits and dialysate circuits of various embodiments. The different types of pumps all operated and produced a working portable or wearable CRRT device, but the embodiments that incorporated a dual channel pulsatile pump wherein the dialysate circuit 134 and the blood circuit 132 were being alternatively pumped in a pulsatile fashion at or about 180 degrees out of phase provided some unexpected, positive results. It was found that the clearance levels of blood toxins across the hollow fiber membrane dialyzer is higher when an alternating, out of phase dual channel pulsatile pump was used with respect to in phase pulsatile pumps or pumps, such as roller pumps and centrifuge pumps were used and which, did not provide as large a pressure differential across the dialyzer's membranes between the dialysate circuit and the blood circuit. Furthermore, unexpectedly the use of the pulsatile pump decreased clogging of the hollow fiber dialyzer membranes due to protein buildup or up, clotting or other fluid-flow inhibitors in experimental devices over experimental configurations that did not incorporate the pulsed pumping provided by a pulsatile pump in both the blood and dialysate circuits.

The mechanisms of solute transport across the membrane of a hollow fiber dialyzer have been studied for more than half a century. Historically, it appears that pioneers of dialytic therapy were well aware of the diffusion phenomena when they designed dialyzers based on counter-current mass exchangers. It was soon realized that convection also played a role as a mechanism in ultrafiltration and "the solvent drag" phenomena. The factors influencing solute transport across semi-permeable membranes have been summarized in various papers including Ronco et al., "Evolution of Synthetic Membranes for Blood Purification," Nephrol Dial Transplant (2003) 18 [Suppl 7]: vii 10-vii 20. In short, blood flow rates greatly affect the clearance of small solutes such as urea, but larger solutes are affected mainly by ultrafiltration rates.

In the past a push-pull hemodiafiltration (HDF) device provided a rapid forward and backward filtration through a dialyzer. This HDF mechanism led to alternating the flow of body fluid and dialysate across a high flux hollow fiber membrane. Although this technique worked, it had various drawbacks. One of the main drawbacks of conventional push-pull HDF devices are the necessity of a disposable blood reservoir bag that was required to prevent flow variation, as well as the difficulty of maintaining a trans-membrane pressure (TMP) across the hollow fiber membranes that would not lead to a collapse of the hollow fibers during back-filtration. One remedy to these push-pull HDF device problems has been to use volume controllers for ultrafiltrate removal and rigid synthetic hollow fibers made out of polyacrylonitrile, polysulfone, and polyamide.

An exemplary wearable or portable artificial kidney or CRRT device 100, as shown in FIG. 1 provides a lightweight, belt-type or small portable device that is battery operated and utilizes the unexpected advantages of a low pulsatile flow rate of 40 to 80 ml per minute of blood and dialysate through a dialyzer filter. Such a device can be used to provide continuous dialysis treatment to patients with End Stage Renal Disease (ESRD) in a manner that may be continuous or substantially continuous for eighteen to about forty-eight hours.

The basic elements of an exemplary wearable or portable CRRT device, as shown in FIG. 1, could be summed and described as comprising the following four main parts or sections. The first section is a dual channel or dual pulsatile pump (or pumps) 124 that propels blood through the device in one channel and dialysate through the device in another channel. Both the blood and dialysate may be pumped at different flow rates. Furthermore, the blood and dialysate are pumped in an out of phase or counter phase pulsatile fashion such that the peak pumping pressure of the dialysate and blood channels occurs at alternating times. A second part is a high flux hollow fiber membrane dialyzer 152 comprising from 0.2 to about 1 square meter ($m^2$) of membrane surface. In tests conducted of an exemplary device, an AN-69 dialyzer was used having about 0.6 $m^2$ of fiber membrane surface. A third part or section of an exemplary embodiment comprises a dialysate regeneration system 122 comprising one to four specially designed powder or particle filled canisters or cartridges containing the same or substantially similar sorbents used in the REDY system used in very large clinic size dialysis machines. The dialysate regeneration system may also include reservoirs 182 of electrolyte additives including magnesium, calcium, potassium and sodium bicarbonate to the ultrafiltrate path, and a pH-control circuit 176 for monitoring and lengthening the usefulness of dialysate flowing through an exemplary device's dialysate circuit. A fourth section or part of an exemplary embodiment may include auxiliary pumps, generally small or micropumps 140 for delivering heparin 142 and perhaps other medications 156 or substances to the blood circuit. An auxiliary pump or valve 186 may also be included for aiding the removal of ultrafiltrate from the dialysate circuit. It is understood that each of these auxiliary or micropumps all are operated at microprocessor controlled 108 or pre-specified flow rates.

It is well known that conventional hemodialysis devices use quasi-steady counter flows of blood and dialysate in a dialyzer. It was believed that such a steady counter-flow of liquids across the hollow fiber membrane in a dialyzer may contribute or be responsible for greater or increased performance in various dialyzers. Using embodiments of the present invention, a study was performed to compare the impact of a pulsatile flow in the transport of solutes in a high flux dialyzer compared with steady or quasi-steady counter flows in a substantially identical high flux dialyzer. Comparative experimental studies and numerical investigations were deployed to clarify and verify the roll of parameters influencing the transport phenomena across a dialyzer's membrane when counter-phased pulsatile flow is used in both blood and dialysate circuits of an exemplary portable or wearable CRRT device as compared to using the same CRRT device with a standard power hungry roller pump commercially used in dialysis equipment. It should be noted that the flow generated by a commercial roller pump somewhat resembles pulsation of either blood or dialysate provided by a pulsatile pump but with a significantly lower amplitude. The following equations have been adopted to assess the clearance and standard weekly urea Kt/V as measures for evaluating the solute removal efficiency of a high flux dialyzer in the comparative investigations.

$$\text{clearance} = \text{Flow} \frac{[\Delta \text{ Solute}]}{[\text{Solute in}]} \quad \text{Equation 1a}$$

$$\text{Standard Weekly} \frac{Kt}{V} = \frac{(\text{Effective Clearance}) \times (\text{Time})}{(\text{total body water})} \quad \text{Equation 1b}$$

Equation 1a can be applied to both the blood side and dialysate compartments of an exemplary dialyzer. Equation 1b accounts for the effects of solute distribution volume in blood, in interstitial space and recirculation.

The comparison study was performed to provide data that explains the enhanced clearances provided by, a dual channel pulsatile pump in an exemplary wearable or portable CRRT device. The experiments and comparison study provided support for the hypothesis that the enhanced clearances of exemplary pulsatile pumped devices are due to counter-phased pulsatile blood and dialysate flows generated by the pulsatile pump(s) along with pulse created washing out effects established by the time-dependent flow inside the hollow fibers of the dialyzer. Such washing-out effects prohibit near-wall accumulation of large molecules. The large molecules may include proteins and other large substances that may be found in a patient's bloodstream but do not readily pass through the fiber membranes into the dialysate.

Figure 2:
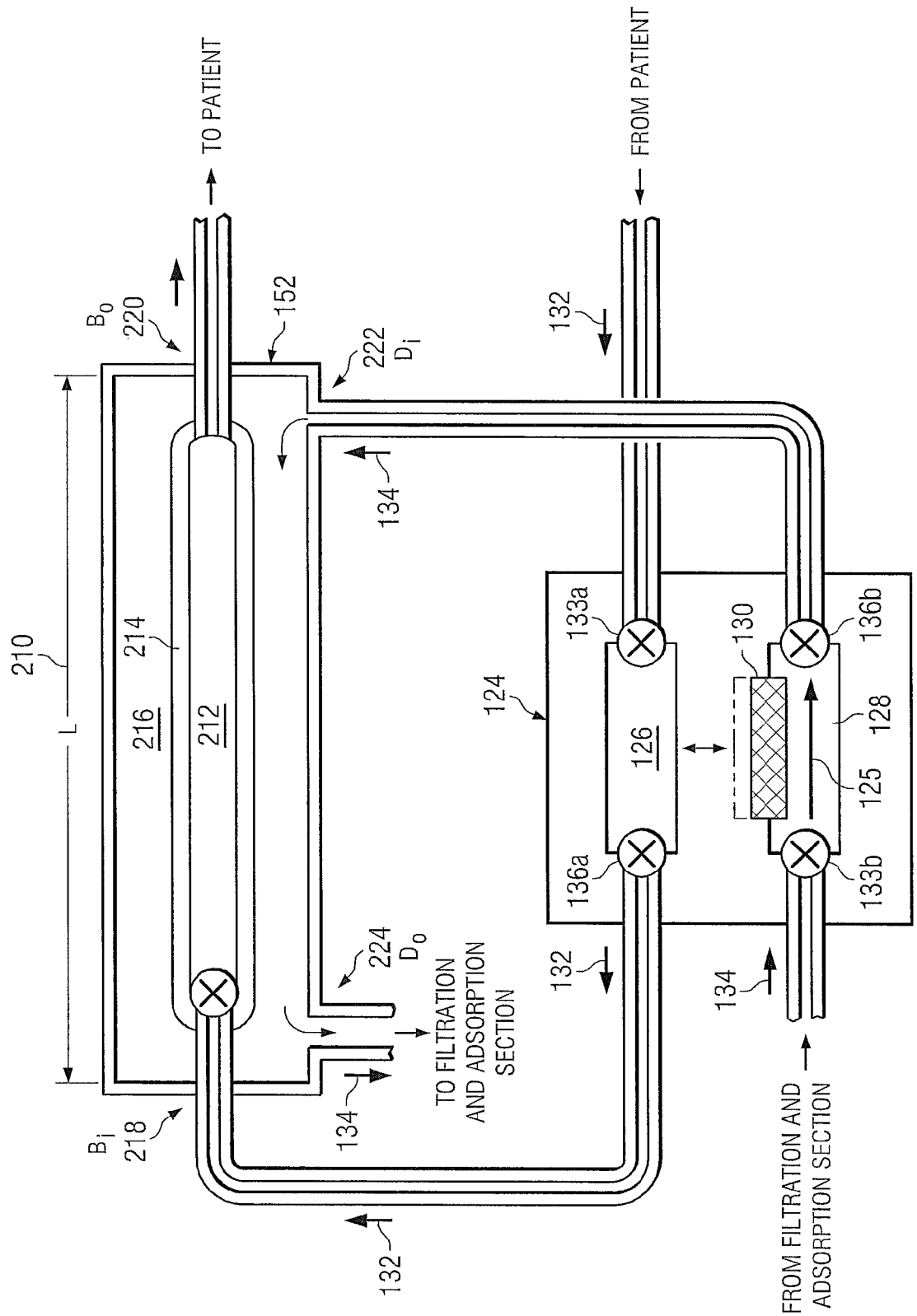
FIG. 2 illustrates a basic configuration of a dual channel pulsatile pump in conjunction with a dialyzer in accordance with various embodiments of the invention.
Figure 3:
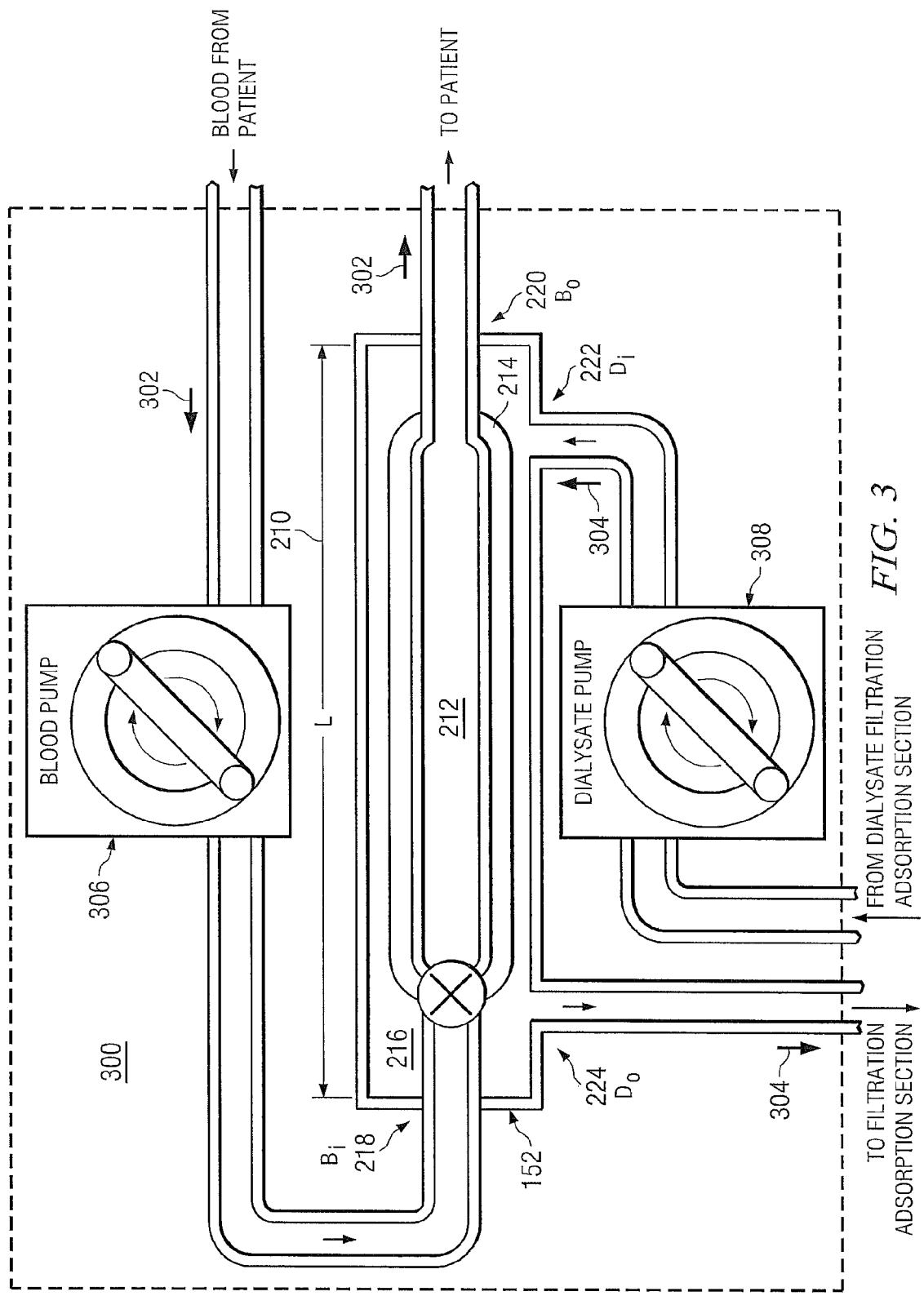
FIG. 3 illustrates a test configuration using a roller pump to pump dialysate and a roller pump to pump blood through fibers in a dialyzer.

Referring now to FIG. 2, an exemplary configuration of a wearable or portable CRRT device in accordance with embodiments of the present invention is shown. This portion of the CRRT device 100 mainly depicts the dual channel pulsatile pump 124 and the dialyzer 152. This figure is provided to help explain the comparative results of experiments and studies being due to the impact of an alternating pulsatile flow of blood in the blood circuit 132 and dialysate in the dialysate circuit 134. The pressure sensors, reservoirs and micropumps and other elements depicted in FIG. 1 are not included in the FIG. 2 to eliminate some figure clutter. Furthermore, FIG. 3 depicts a similar portion of a wearable or portable CRRT device as in FIG. 2, except that large, heavy, power-inefficient roller pumps or centrifuge pumps (standard pumps) are used to pump blood through the blood circuit 302 and dialysate through the dialysate circuit 304. This dual standard pump configuration 300 is, like FIG. 2, drawn without including pressure sensors, micropumps, reservoirs and various other details depicted in FIG. 1.

Referring to both FIGS. 2 and 3, the dialyzer 152 is the same in both configurations. The particular dialyzer 152 is shown with only one hollow membrane lumen 212 extending the length "L" 210 of the dialyzer 152. It is understood that in a real exemplary or actual dialyzer there would be hundreds of hollow lumens (fibers) extending the length L of the dialyzer for the blood to pass through in the blood circuit 132. The membrane 214 on the outside of the membrane lumen 212 is the membrane through which mass transport of solutes, including toxins, cross or pass through the membrane 241 from the blood circuit 132 to the dialysate circuit 134. Dialysate flows through the dialyzer via the dialysate compartment 216. The blood flowing in the blood circuit 132 enters the dialyzer via the blood input 218 ($B_i$), travels through a plurality of lumen membranes 212 and exits the dialyzer via the blood output 220 ($B_o$). Similarly, in the dialysate circuit dialysate flows into the dialysate compartment 216 via the dialysate input or inlet 222 wherein the dialysate travels the length 210 of the dialyzer and exits the dialyzer compartment 216 at the dialysate output or outlet 224 and continues on through the remaining portion of the dialysate circuit 134.

Referring to FIG. 2 specifically, the dual channel pulsatile pump 124 uses a 2-5 watt DC motor to move the pushing element 130 in an oscillating fashion back and forth against the flexible blood compartment 126 and dialysate compartment 128. In FIG. 2, the pushing means 130 is shown to be pressing against the dialysate flexible chamber 128 thereby pushing dialysate in the direction of the arrow 125 within the chamber through exit valve 136b while the input valve 133b of the dialysate chamber is held in a closed position. The pushing member then moves toward the flexible blood chamber 126 decompressing the flexible dialysate chamber 128. Decompression of the dialysis chamber 128 closes the dialysate output valve 136b and opens the dialysate input valve 133b. Meanwhile, as the pushing mechanism 130 presses against the flexible blood chamber 126 within the dual channel pump, the blood within the chamber is forced to exit the output blood valve 136a while the input blood valve 133a remains closed. In this manner, an exemplary dual channel pulsatile pump provides counter-phased or alternating phased or 180 degrees out of phase pulsatile flows of the appropriate fluids through the blood and dialysate circuits. It is understood that a pulsatile pump may be manufactured in a variety of ways such that two chambers of fluids can be made to pump at alternating times. Such counter flow or alternating pump peak moments may be 180 degrees+/−about 90 degrees out of phase. Exemplary embodiments do not require that the dialysate flow and the blood flow be at the same rate in ml per minute due to the two fluids having different viscosities. Furthermore, the dual channel pulsatile pump may pump the fluids in the same or opposite directions. Furthermore, the pumps may be comprised of two separate pumps so long as the alternating aspect of the pulsatile pumping is maintained. In other words, as one chamber of the exemplary pulsatile pump is filling with fluid that the other chamber of the pulsatile pump is propelling fluid out of its chamber and into its designated fluid circuit. Such an alternating pump mechanism allows for a peak pressure to be obtained in one circuit near the same time that a minimum fluid pressure is obtained in the other fluid circuit.

The dialyzer 152 may comprise fibers having from 0.2 to about 1 $m^2$ in membrane surface area about the hollow membrane lumens.

Referring now to FIG. 3, a standard roller pump 306 is used to pump blood through the blood circuit 302 while a similarly standard dialysate pump 308 was used to propel dialysate to the dialysate circuit 304. The blood pump 306 and dialysate pump 308 are similar in structure and design to roller pumps used in prior art dialysis machines. During comparisons of the two configurations (FIG. 2 and FIG. 3) ultrasonic equipment was used to visualize blood and dialysate flows through their respective circuits. Furthermore, pressure sensor and measuring equipment were used to measure blood input pressure at the blood input $B_i$ of the dialyzer 218 and blood output pressure at the blood output $B_o$ of the dialyzer 220 as well as dialysate input pressure at the input of the dialyzer 222 and dialysate output pressure at the output of the dialyzer 224. In the comparative experiments, dialysate and blood were pumped via the dual pulsatile pump at flow rates of about 40, 50, 60 and 80 ml per minute (pulsatile). Furthermore, the pH of the dialysate was sensed via a pH probe located in a position after the filtration section, but prior to the dialysate being pumped into the dialyzer. Appropriate additives such as sodium bicarbonate were added to the dialysate to maintain the pH of the dialysate between 7.3 and 7.5.

Figure 4:
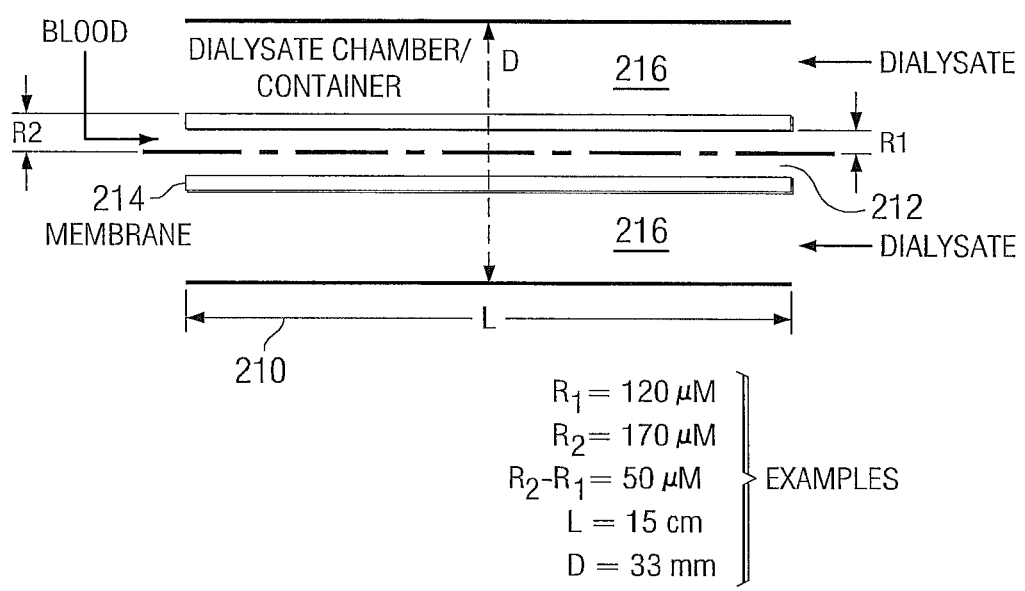
FIG. 4 illustrates a single hollow fiber and adjacent dialysate within an exemplary dialysate chamber of a dialyzer in accordance with an embodiment of the invention.

The dialyzer 152 contained approximately 4,500 lumen membranes each having a length L 210 of about 15 cm. FIG. 4 shows the length L 210 of 15 cm and the inner radius of each lumen membrane R1 being about 120 micrometers. The outer radius of the exemplary lumens R2 was about 170 micrometers. Thus, the thickness of the membrane 214 about the lumen is equal to R2−R1 or about 50 micrometers thick. The diameter of the hemofilter was about 33 mm. FIG. 4 is obviously not drawn to scale but is provided to show a single hollow fiber 212 extending a length 210 of the dialyzer having blood flowing within its inner radius R1 and dialysate flowing outside of the outer radius R2 of the fiber 212 in the dialysate chamber or compartment 216. Solute will be transported from the blood in the center of the fiber lumen 212 through the membrane 214 and into the dialysate compartment 216.

For the standard or roller pump configurations, pumping rates were made similar to the pulsatile pump rates provided in the dual pulsatile pump embodiment such that the blood and dialysate flow rates in the configuration of FIG. 3 with the standard pumps 306 and 308 were also about 40, 50, 60 and 80 ml per minute.

Comparisons of the input and output pressures of the dialyzer's dialysate inputs and outputs as well as the blood inputs and outputs were compared in both experimental configurations. Furthermore, the clearance of toxins and solutes were carefully studied based on samples of dialysate going in and coming out of the dialyzer as well as samples of blood going in and out of the dialyzer.

Unexpected clearance results occurred and were measured in the comparative dialysis configurations using different pumps. In particular, the clearance of the pulsatile pump configuration of FIG. 2 was significantly higher than the clearance of the standard roller pump configurations. Clearance is referred to as the overall removal or clearance of toxins and solutes from the blood as it passes through the dialyzer. Furthermore, ultrafiltration of the blood occurred with respect to energy required, more efficiently using the exemplary dual channel pulsatile pump configuration than using a standard roller or centrifocal pump configurations. Although measurements could only be taken at the inputs and outputs of the dialyzer, speculation can be made to try to explain what is occurring within the dialyzer between the dialysate circuit and the blood circuit and across the fiber membranes. The results of the comparison are described in more detail below.

The results of testing configurations using exemplary dual channel pulsatile pump 124 in comparison with two standard roller pumps one for blood 306 and one for the dialysate circuit 308. Flow rates and pressures were sensed at the dialyzer blood input 218 and dialyzer blood output 220. Pressure and flow readings were also sensed at the dialysate input 222 and dialysate output 224. Flow rates were measured using high resolution Doppler ultrasonography and pressures were sensed using micropressure sensors. Results of the testing were divided into two categories; a first category was the ultrafiltration results and the second category was the clearance results. It was determined that the ultrafiltration output of the dialyzer was found to be mathematically proportional to the pressure difference between the blood within the dialyzer lumens and the pressure of the dialysate in the dialysate compartment 216. The measurements were taken during a steady-state operation of an exemplary embodiment; thus, there was a preload pressure in the inlet to an afterload pressure in the outlet from the pumps. The preload was induced by the pump head pressure and the afterload was created by the resistance of the dialysate filtration and absorption section 122 of an exemplary embodiment.

Figure 5A:
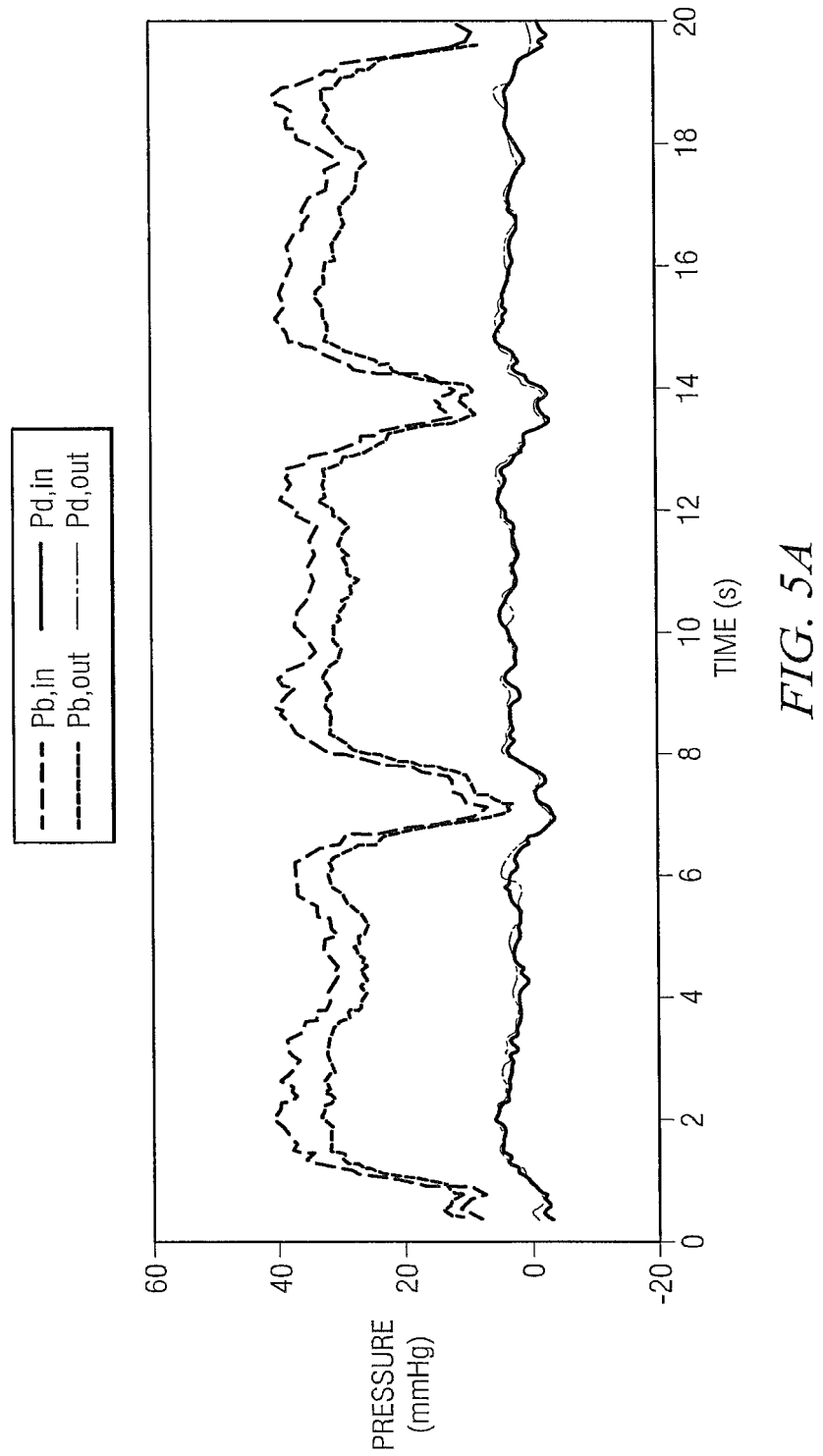
FIGS. 5A and 5B provide sample experimental result measurements of: a) input and output dialyzer pressures and b) input and output dialyzer flow rates for a combination roller pump and centrifugal pump configuration used in an experimental comparison dialysis device.
Figure 5B:
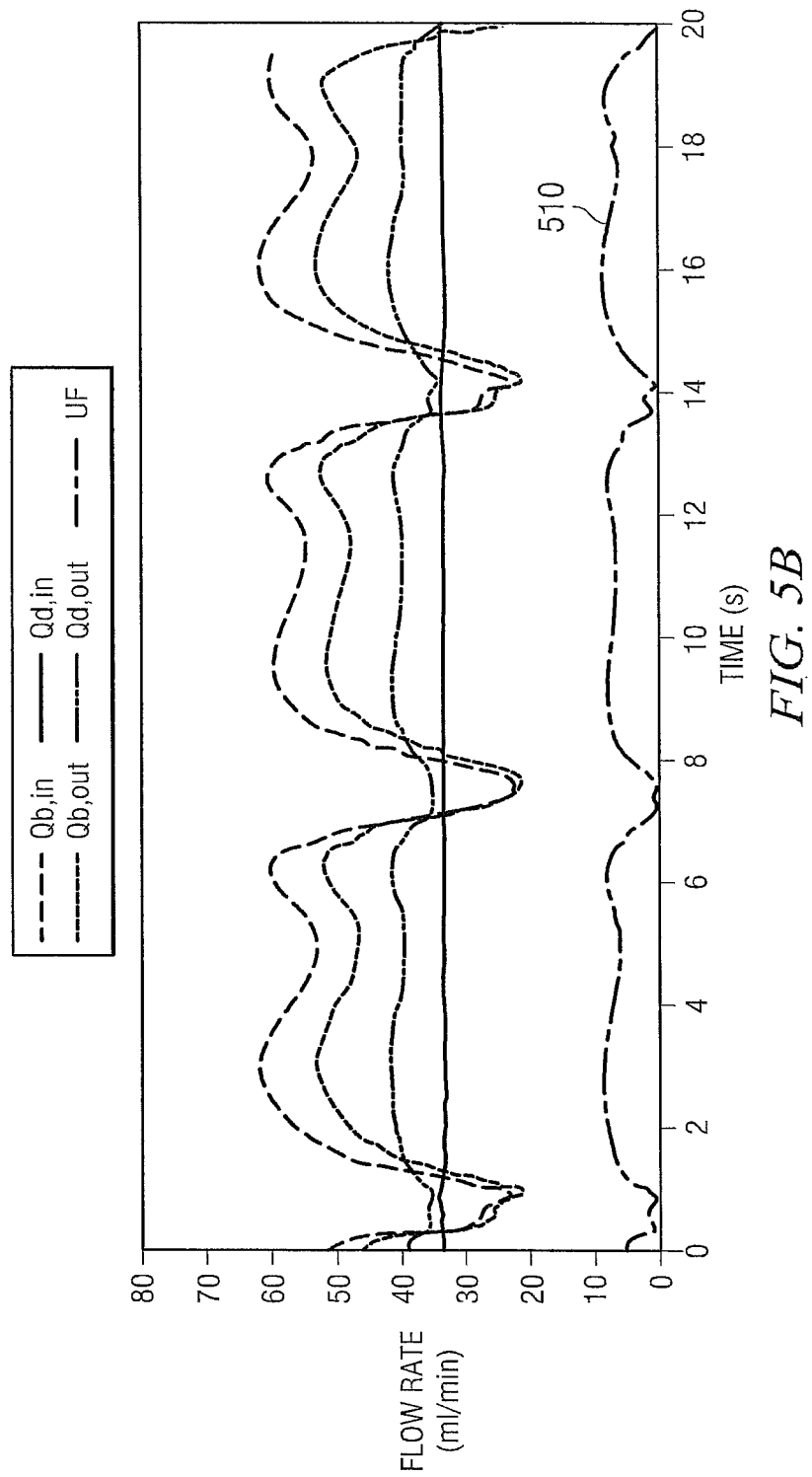
Figure 6A:
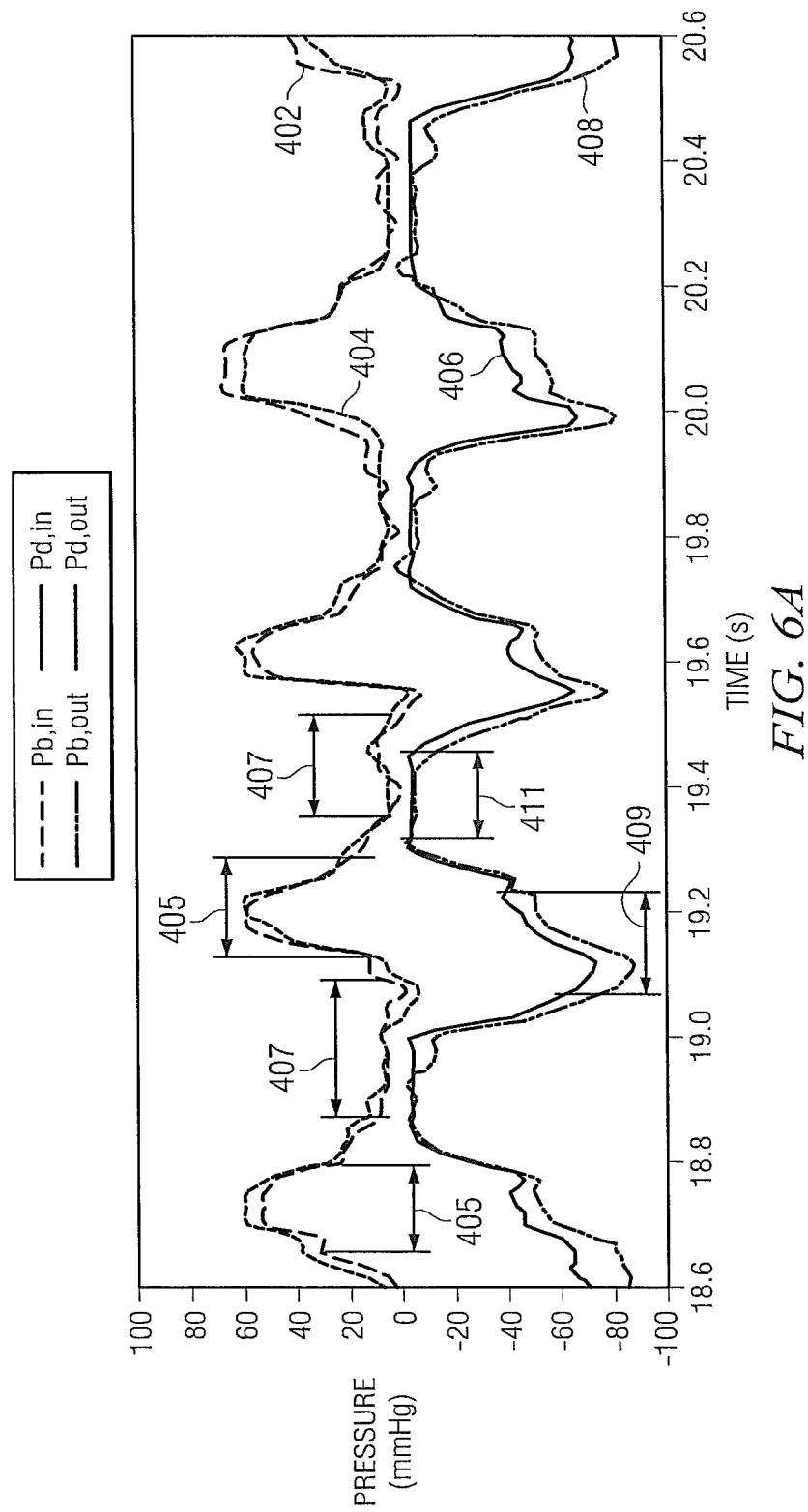
FIGS. 6A and 6B provide sample experimental result measurements of: a) dialyzer inlet and outlet pressures and b) dialyzer inlet and outlet flow rates for an exemplary dual channel pulsatile pump used in accordance an embodiment of the invention.
Figure 6B:
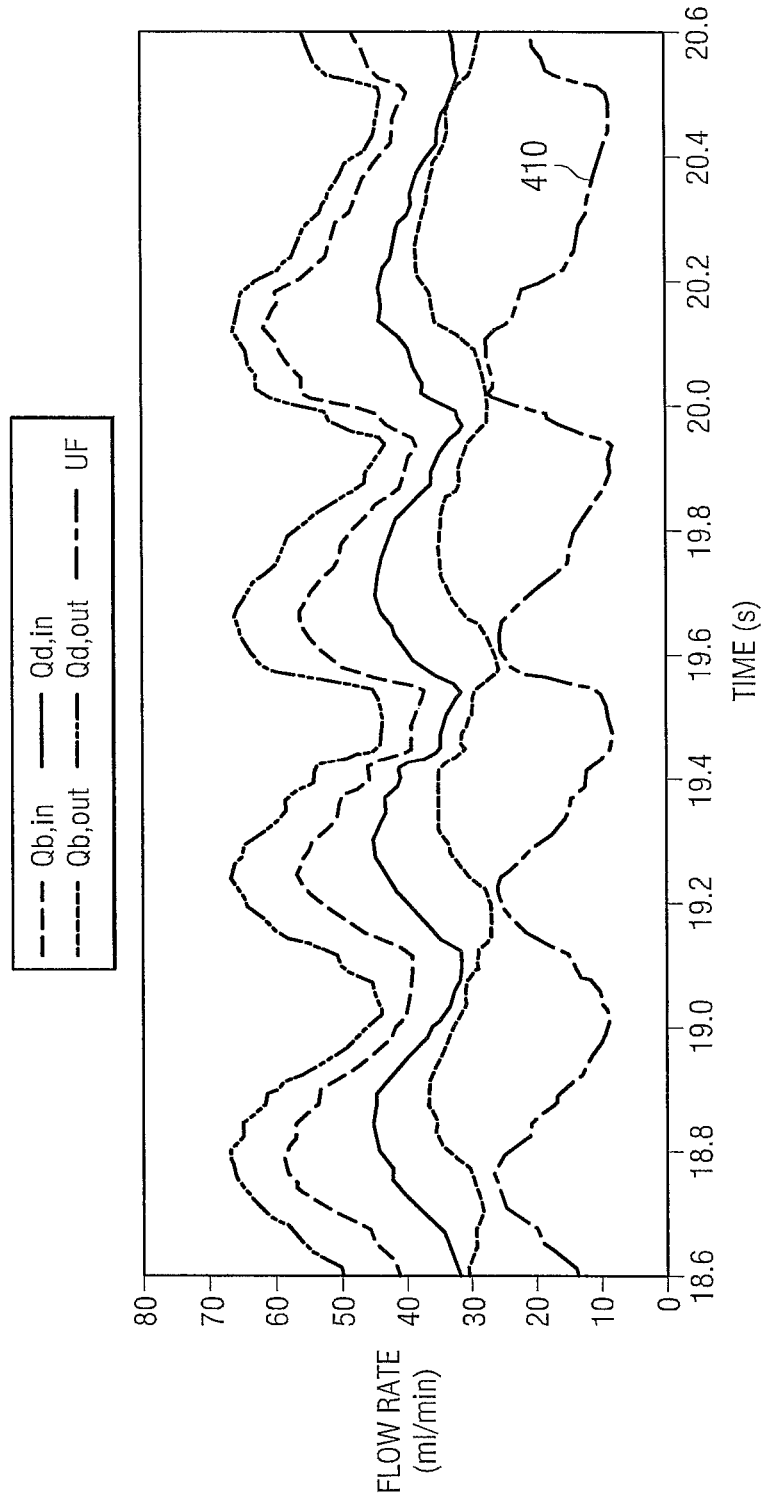

The ultrafiltration characteristics are depicted with additional experimental results in FIGS. 5A, 5B and FIGS. 6A, 6B. In FIGS. 5A and 5B, experimental results providing pressures and flow rates at the dialyzer inputs (inlets) and outputs (outlets) are shown along with an ultrafiltration output for the roller pump configuration. In FIGS. 6A and 6B pressures and flow rates for the input and outputs of the dialyzers are shown along with the ultrafiltration output for the exemplary pulsatile pump configuration. In each situation, the pressures and the flow rates at the inlets and outlets of the dialyzers along with the ultrafiltration rate is shown. The pulsatile pump configuration in FIG. 6A generates a time-dependent flow of blood and dialysate through the dialyzer. In particular, the input and output peak or maximum blood pressure pulses 402 and 404 are generally about 180 degrees out of phase with the dialysate input and output peak or maximum pressures 406 and 408, respectively. The time duration or length of the high blood pressure portion 405 of the periodic blood pulse flow may be longer or shorter than the length of the low pressure portion 407 the periodic blood pulse flow. The time duration of the high and low blood pressure portions may have a ratio of from about 4:3 to about 3:4. Ideally, the ration would be 1:1, but is not specifically necessary for good clearance results. The blood pressure at the input 402 and blood pressure at the output 404 of the dialyzer for the pulsatile configuration ranged from about 0 to +60 mmHg. Meanwhile, the dialysate pressure at the input 406 and dialysate pressure at the output 408 are at or near their pressure minimums of between about −90 to −60 mmHg when the pressure of the blood is near its peak of between 55 and 60 mmHg The time duration of the dialysate pressure minimums 409 is similar in length and overlaps fifty percent (50%) or more of time duration of the blood pressure maximum duration 405. Furthermore, the dialysate input and output pressure 406, 408 are at their maximums of about 0 mmHg while the pressure of the pulsed blood flow at the input 402 and output of the dialyzer 404 are at their minimum pressures of about 0 to 10 mmHg thus shown in FIG. 6B. The time duration of the dialysate input and output pressure maximums 411 overlap at least about fifty percent (50%) of the pulsed blood pressure during its minimum time duration 407. In FIG. 6b, one can see that when the difference between the blood pressures at the input and output 402, 404 is greatest with respect to the pressures of the dialysate at the input and output 406, 408, the flow of dialysate 410 is at or near its maximum. It is also important to note that the difference in pressures between the dialysate flow through the dialyzer and the blood flow through the dialyzer appears, at the input and outputs of the dialyzer to be in a range of about 120 mmHg+/−20 for a maximum difference and 10+/−10 mmHg for a minimum pressure difference.

Figure 15:
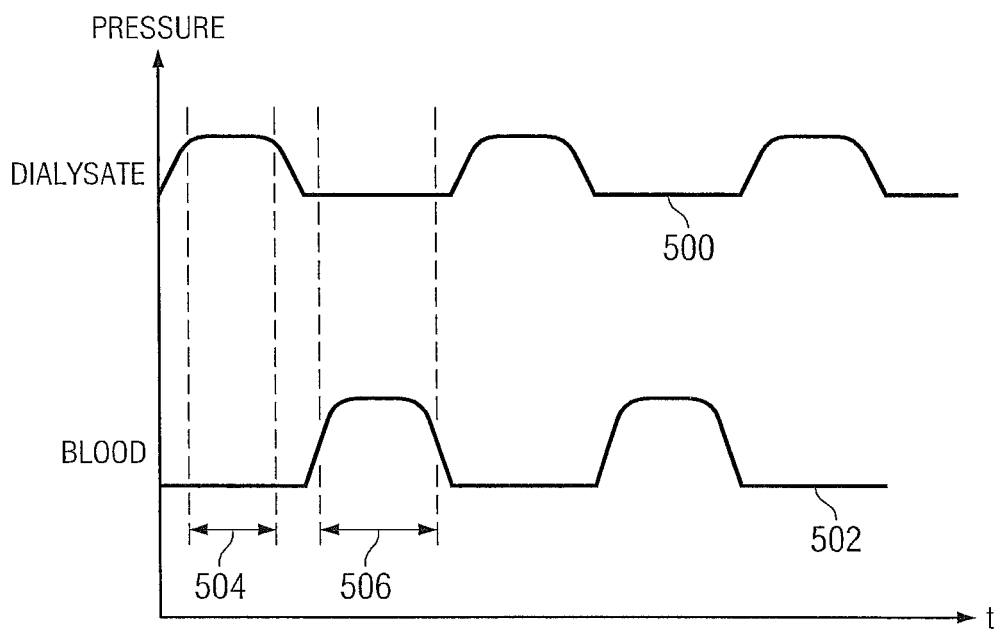
FIG. 15 is a graph of an exemplary blood and dialysate pressure or flow over time produced by a single dual channel pulsatile pump or two synchronized pulsatile pumps.

Looking at FIG. 15, an ideal, yet easier to understand graph of the output pressures of the blood channel pulsatile pump and the dialysate channel pulsatile pump is shown. The periodic dialysate flow 500 has a maximum pressure duration period that overlaps the minimum pressure duration period of the periodic blood flow 502. This over lap 504 coincides with the over lap of dialysate maximum duration portion 411 and blood minimum duration period 407 of the actual experimental results in FIG. 6A. Furthermore back in FIG. 15, the minimum pressure duration portion of the dialysate flow 500 overlaps or coincides in time with the maximum pressure duration portions of the periodic blood flow 502. This overlap 506 coincides with the overlap of the dialysate minimum pressure duration portion 407 and the blood maximum pressure duration period of the periodic blood flow 405 of the actual experiments results of FIG. 6A. The head pressures caused by the filtration and adsorption portion 122 and the blood and dialysate inlet and outlet ports appear to have established the unexpected increased TMP across the fiber membranes that results in a enhance clearance of toxins from the blood flowing through the dialyzer. The enhanced clearance is achieved using very little power into the pulsatile pump or pumps that may be incorporated into embodiments of the invention.

In FIG. 15, it should also be noted that the lengths or time durations of the high pressure pulses (and high flow rates) for the dialysate fluid flow 500 should be substantially the same as the lengths or time durations of the low pressure pulses (or low flow rates) of the blood flow 502. The ratio of the dialysate high pressure pulse duration to the dialysate low pressure pulse duration should have a ration range that is between 3:4 and 4:3. It follows that the lengths of the dialysate low pressure pulses (and low flow rates) should be substantially the same as the length or time duration of the high pressure blood pulses (or high flow rates). This is useful in embodiments of the invention for synchronizing two separate pulsatile pumps. Such dual separate pulsatile pumps could be synchronized using digital stepper motors or by having digital sensors sensing rotational positions of a motor and adjusting motor speeds with a motor controller circuit.

Looking at FIG. 5A, the roller pump configuration, one immediately notes that the pressure difference between the blood input and output and the dialysate input and output has a small pressure differential range. The difference between the average of the input and output blood pressure, at any point in time, with the average of the dialysate input and output pressure, ranges from about 0+/−5 mmHg and about 35+/−7 mmHg of differential pressure. FIG. 5B shows a significantly lower amount of ultrafiltrate 510 being produced by the roller pump configuration over time than being produced by the pulsatile pump configuration of the exemplary embodiment shown in FIG. 6b. Also note that although the roller pump provides some element of pulsation in the blood flow, the decreased pressure part of the roller pump's pulse is much shorter than the decreased pressure part of the blood pressure pulse in the pulsatile pump configuration of FIG. 2. Thus, the peak pulse/min pulse duration of pulsatile pump configuration are substantially similar in time length (i.e., +/−10%). Furthermore, the maximum amount of pressure provided by the roller pump configuration, at similar blood flow rates, as in the pulsatile pump configuration is a longer pulse than the pulsatile pump configuration. The blood pressure at the input and output of the dialyzer achieved with the roller pump configuration is generally about 20 mmHg or more lower than the peak pressures of the blood pressures sensed at the input and output of the dialyzer in the pulsatile pump configuration. This was an unexpected result as the pulsatile pump uses only about 3 watts or less of energy to produce the flow rates provided wherein the roller pumps of the roller pump configuration requires twenty to fifty watts of energy to provide the similar blood flows rates and pressures as shown in FIG. 5.

Referring back to FIG. 6b, one can see that the flow rate through the dialyzer with the pulsatile pump configuration varies in a somewhat or near sinusoidal pattern for both the dialysate and blood flow. The maximum and minimum flow rates of the dialysate and blood flow (peak to peak) range from about 5 ml per minute to about 20 ml per minute. As such, the fluids traveling through the dialyzer are accelerating in decelerating in a regular pulsatile pattern. Conversely, the flow rates shown in FIG. 5B in the roller pump configuration tend to maintain a steady state for about 4 seconds and then decelerate and accelerate quite rapidly in a negative pulse for a period of about 1 second. As such, the acceleration and deceleration within the roller pump configuration is very short-lived when compared to the steady state pulse of the same.

Figures 7, 8:
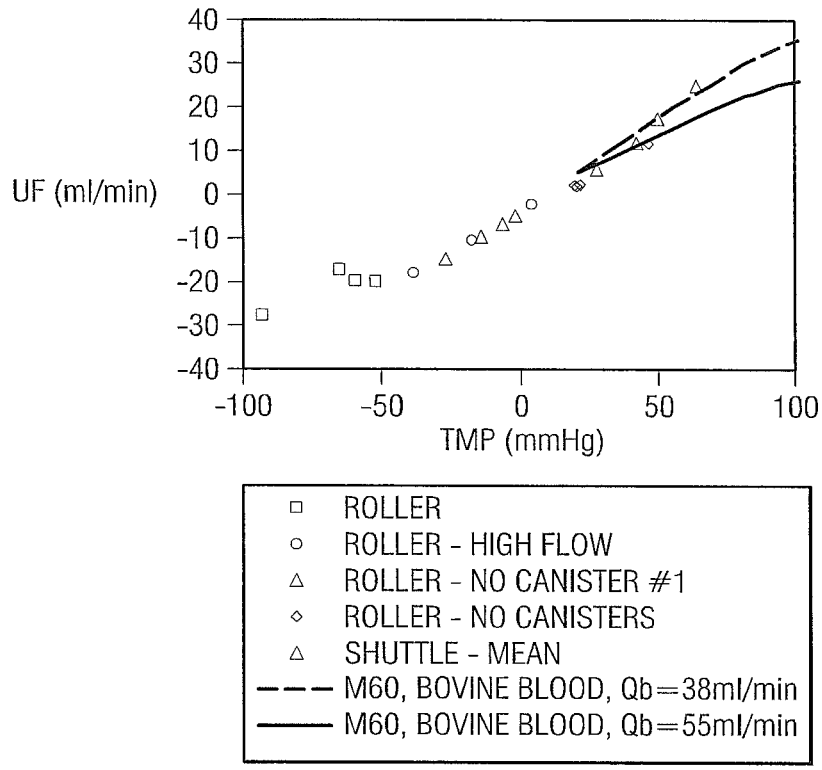
FIG. 7 depicts a graph that reveals experimental result measurements of the relationship between ultrafiltration and a modeled Trans Membrane Pressure (TMP) across a fiber within a dialyzer for both a roller and pulsatile (shuttle) pump configurations.
FIG. 8 depicts a chart providing a comparison of exemplary experimental results for a roller pump configuration and an exemplary pulsatile pump configuration.

FIG. 7 provides the ultrafiltration rate when compared to the peak transmembrane pressure (TMP). The TMP is the difference in pressure between the blood within the lumen of the dialyzer 212 and the dialysate within the dialysate compartment 216 of the dialyzer filter. As shown the ultrafiltration rate depends greatly on the peak TMP; however, the ultrafiltration dependence on TMP appears to be nonlinear. This finding is also unexpected as the present practice and understanding of ultrafiltration in a dialyzer is believed to be linear relationship with respect to TMP. This unexpected result of a nonlinear ultrafiltration dependence on TMP was shown by a best fit of a second order polynomial to the experimental data points of the roller pump configuration of FIG. 3 and separately for the exemplary dual pulsatile pump configuration of FIG. 2. The slopes obtained for the pulsatile pump configuration were larger than the slopes obtained for the roller pump configuration but, only by a small margin. The small margin of improved ultrafiltration capability may be very significant as an exemplary wearable or portable ultrafiltration device is worn or used on a patient for extended periods of time. The significance is that additional ultrafiltrate may be removed from a patient's blood using a pulsatile pump configuration, which requires much less energy than a roller pump or centrifugal pump configuration and provides substantially similar blood and dialysate flow rates through a dialyzer. Furthermore, the push-pull-like movement created by the pulsatile pumps and the associated washing effect on the inner walls of the fibers may also play a role in the added efficiency of exemplary embodiments of the invention.

The experimental results of the clearance levels provided similarly unexpected results via the experimentation. In the experimental setup of the exemplary embodiment using a dual channel pulsatile pump, the dual channel pulsatile pump was operating at a pulsatile rate of about 2 hertz. It is understood that a larger pulse chamber tubular pump chamber or smaller pump chamber would enable a pulsatile pump to operate an oscillation frequency of between about half a hertz to about 4 hertz. Pulsatile pumping at a rate higher than 4 hertz might be damaging to the blood cells in the blood flow, but would probably be acceptable for the dialysate circuit. It is believed that the best pulsed flow rate for the blood and dialysate should be between 1 and 3 hertz such that the liquids flow at rates between about 20 and 100 ml/min.

In the dialysate compartment, the dual channel pulsatile pump establishes a relatively large pulsed negative pressure leading to a large transmembrane pressure (TMP) having a peak of about 140 mmHg, but generally ranging between around 70 and 120 mmHg. A TMP caused by the pulsatile or shuttle pump is more of a general approximation due to the imperfect out of phase or counter-phased pulses of fluids (i.e., blood and dialysate) flowing through the dialyzer and opposing directions. Furthermore, pressure measurements were only made at the inputs and outputs of the dialyzer because the actual TMP across a membrane inside the dialyzer could only be computer modeled.

The ultrafiltration rate in the pulsatile pump embodiment is unexpectedly large relative to the blood flow rate (30-50%). It was determined that in a pulsatile pump configuration, the convection urea transfer is about 31% of the total urea transfer while in the roller pump configuration, the convection urea transfer was only about 17%. It is believed that the larger convection contribution to the urea transfer in the pulsatile configuration is a significant part of the reason why the exemplary pulsatile configuration is a superior configuration for a wearable or portable CRRT or artificial kidney design. FIG. 10 depicts the difference in the ratios of convective urea flux to the total urea flux across a membrane. Here it is easy to see the additional convective urea flux provided in the pulsatile pump configuration across the axial length of the dialyzer.

Referring to FIG. 8, a quick comparison of a roller pump configuration and an exemplary pulsatile pump configuration is shown. The blood flow ($Q_{b,in}$), into both the dialyzer of the roller pump and pulsatile configuration as well as the dialysate flow ($Q_{d,in}$) are both similar flow rates. The test results show that the ultrafiltration from the pulsatile pump provided more than twice the amount of ultrafiltrate (UF) for similar flow rates of the blood and dialysate into the dialyzer. Furthermore, the differential pressure between the pressures of the blood coming out of the dialyzer with respect to the pressure of the dialysate coming out of the dialyzer produced a much higher peak TMP in the dialyzer using the exemplary pulsatile pump configuration.

Figure 9A:
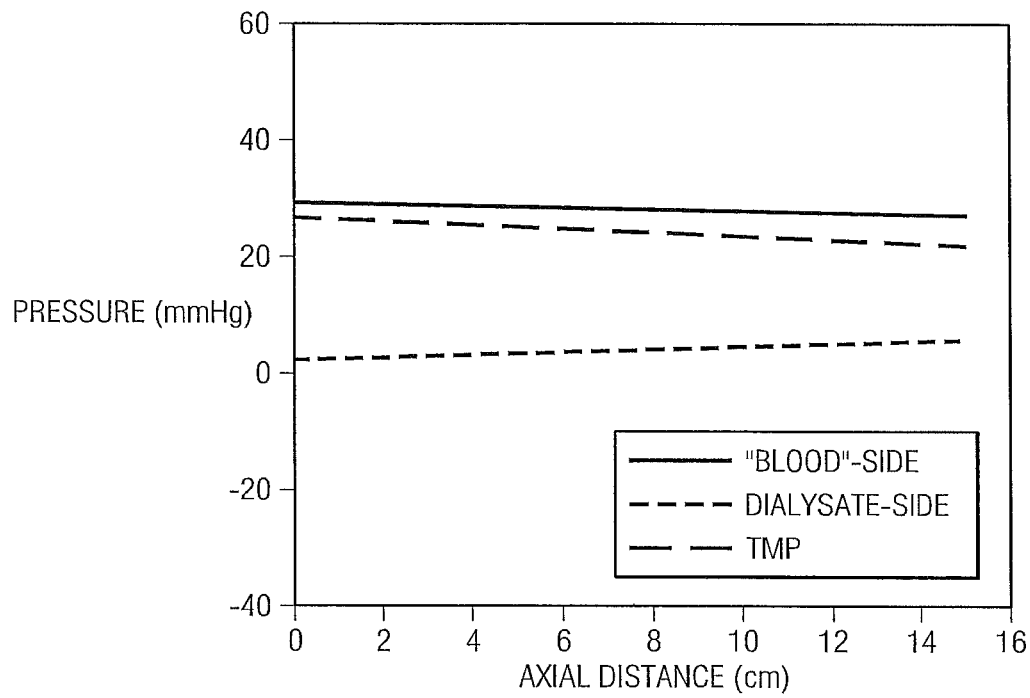
FIGS. 9A and 9B provide graphs illustrating experimentally calculated and estimated blood flow, dialysate flow and Trans Membrane Pressures over the axial length of a dialyzer for a configuration with roller pumps and a configuration with pulsatile or pulsed pumps.
Figure 9B:
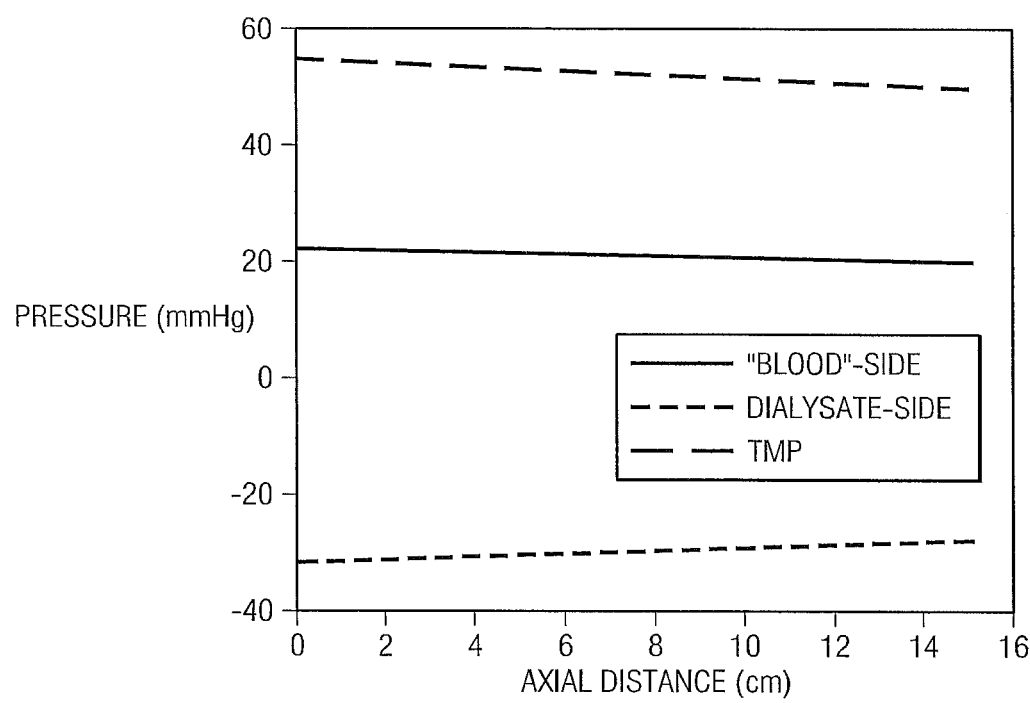

FIGS. 9A and 9B graph a calculated pressure distribution along the axial distance L 210 of the dialyzer in both the roller pump configuration and an exemplary pulsatile or shuttle pump configuration. The maximum pressure distribution is shown. The pulsatile pump configuration shows that on the dialysate side, the pressure increases from about −32 mmHg at the dialysate output side of the dialyzer and it increases to about −28 mmHg at the dialysate input side of the pulsatile pump at about 15 cm. The pressure of the blood at the blood input side of the dialyzer decreases slightly from about 23 mmHg to about 20 mmHg at the output side of the dialyzer. Thus, producing an unexpectedly high peak TMP ranging from between 48 to about 55 mmHg across the axial distance between the dialysate and the blood flows of the dialyzer. FIG. 9A indicates that the maximum TMP in a dialyzer using the roller pump configuration is much lower, about 50% or more, than the pulsed maximum TMP established in the exemplary pulsatile pump configuration.

Figures 13, 14A:
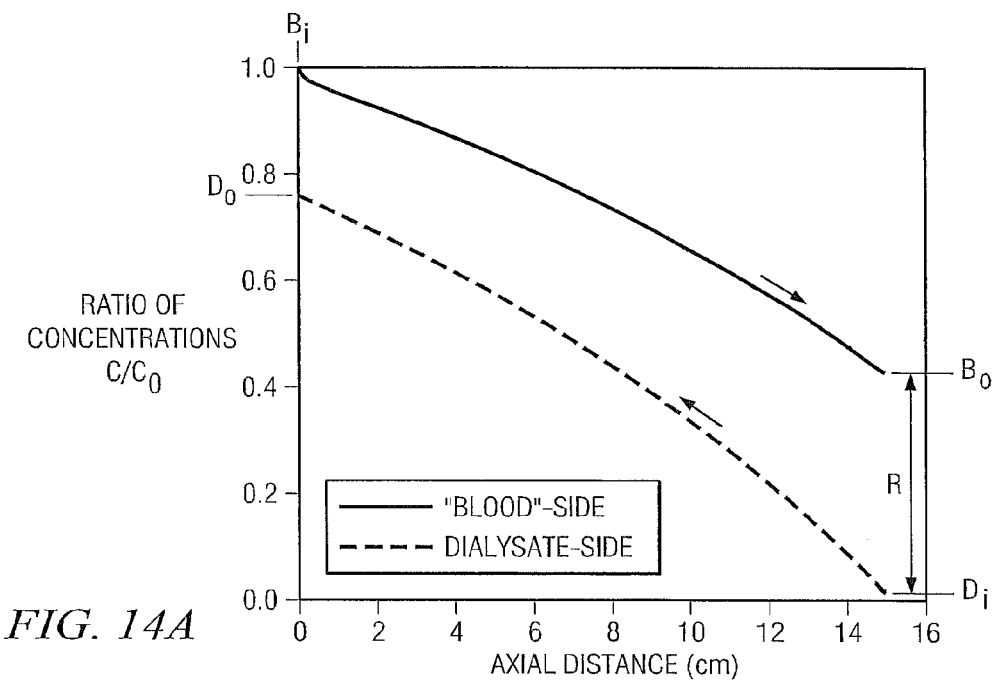
FIG. 13 provides a chart that provides experimental and numerical results for potassium clearance with a roller pump and an exemplary pulsed pump design for various blood and dialysate fluid flow rates.
FIGS. 14A and 14B provide a graph of the relative concentration distribution $C/C_o$ along the axial length of an exemplary dialyzer for the dialysate inlet and the blood outlet in a roller pump configuration and an exemplary shuttle or pulsatile pump configuration.

FIGS. 11, 12 and 13 provide comparisons of the urea clearance, creatine clearance and potassium clearance achieved in the roller pump configuration and an exemplary pulsatile pump configuration of a wearable or portable CRRT or artificial kidney device. It is noted from FIGS. 11, 12, and 13 that for a similar dialyzer input flow rate at the blood input 218 and the dialysate input 222, the TMP and resulting clearance of the urea, creatine and potassium is always greater in the exemplary pulsatile pump or pulsed flow configuration of the exemplary embodiment.

Based on detailed studies and numerical investigations, it is determined that the flow of solutes across a dialyzer membrane varies depending upon the pumping mechanism used to move the dialysate and blood through the dialyzer. In particular, it has been determined that the use of a dual channel pulsatile pump configuration, wherein one pumping channel is for dialysate and a second pumping channel is for blood and where the channels are pumped alternately, counter-phased, or 180+/−90 degrees out of phase, provides a superior ultrafiltration function and clearance of solutes from blood with respect to previously used roller pump and centrifuged pump configurations. By use of experimental and numerical processes, the parameters influencing the transport phenomena across the dialyzer membrane, when counter-phased pulsatile flows are used in both the blood and dialysate compartments of the dialyzer, exemplary embodiments provided unexpected superior ultrafiltration and clearance of toxic solutes from the blood over more expensive, heavy and power-inefficient roller and centrifugal pumps configurations. The results of the exemplary dual channel pump configuration have been compared with a configuration using standard roller pumps or centrifuge pumps that are used in conventional dialysis equipment. Even though the flow of dialysate and blood generated by a roller pump flow resembles a pulsatile flow, a lower amplitude flow and pressure is provided by a roller pump and its flow pulse is much longer than its non-flow or zero pressure pulse on the roller pump. Conversely, the pulsatile pump provides a substantially equally divided flow/high pressure pulse and no-flow/low pressure pulse.

The use of an exemplary dual channel pulsatile pump utilizes important, newly uncovered discoveries with respect to flow and pressure behavior of certain fluids, such as blood and dialysate as they pass through a dialyzer. Furthermore, improved clearance is established for urea creatine and potassium thereby allowing the exemplary pump system to operate at a slower rate for longer periods of time and use a mere 3 to 5 watts of energy to operate the pumping. Furthermore, when using an exemplary pulsatile pump configuration with the filtration and absorption section of an exemplary wearable or portable CRRT device substantially twice the TMP (100-140 mmHg) was established across the membrane when compared with the TMP established with a roller pump or centrifocal pump configuration. The reason for the improved TMP in exemplary embodiments is due to the counter-phased pulsatile flow of the blood and dialysate through the dialyzer establishing the difference in pressures between the blood within the fiber lumens and the dialysate chamber of the dialyzer.

Additional advantages of the exemplary dual channel pulsatile configuration for a wearable or portable CRRT device are that the relationship between the amount of ultrafiltration and the TMP is not linear, as previously understood a roller and centrifuge pump configurations. Instead the relationship between ultrafiltration and TMP builds to a nonlinear second order differential equation.

Figure 14B:
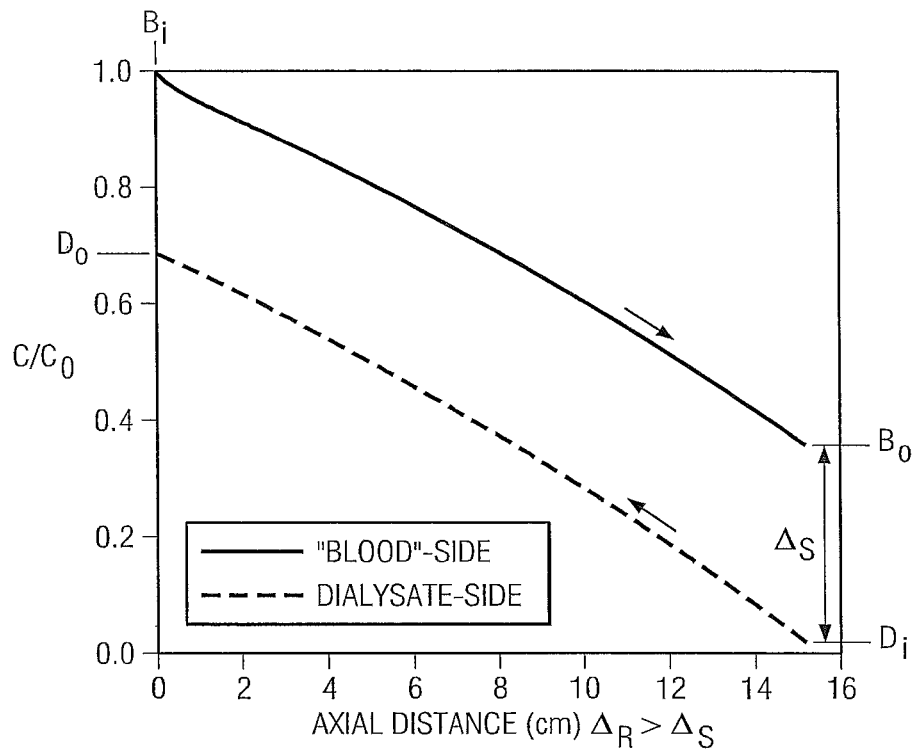

It is important to note that one of the important aspects of the dual channel pulsatile pump configuration is its high efficiency in removing urea, creatine and other solutes from the blood. FIGS. 14A and 14B show how the relevant concentration of solutes is transferred across the membrane over the axial length of a dialyzer with the blood and dialysate flowing opposite directions there through. In FIG. 14A the roller pump configuration is shown wherein the relative concentration drops off for the dialysate indicating that less solute is being transferred across the membrane at the blood output side of the dialyzer with respect to the blood input side of the dialyzer. Conversely, in FIG. 14B, the relative concentration distribution or transfer of solutes from the blood to the dialysate is more linear and does not drop off. It is believed the reason for this more evenly distributed distribution of solute transfer through the membrane and along the length of a lumen fiber in a dialyzer is due to the increased ultrafiltration across the membrane. The higher ultrafiltration rate caused by the higher TMP across the membrane (due to the alternating pulsatile pumping of the dialysate and blood) results in enhanced convective forces which thereby result in better mass transfer of solute across the membrane along the entire axial length of the fiber lumen inside the dialyzer. With the exemplary dual channel pulsatile pump configuration, convection attributed to the 31% clearance of urea while in the roller pump configuration the lack of the additional convection limited the urea transfer to a mere 17%. Experimentation showed that the exemplary pulsatile pump configuration provided a 31% increase in convective mass transfer over the roller pump configuration. The exemplary high TMP created by the dual channel pulsatile pump configuration of an exemplary embodiment provides enhanced clearance and ultrafiltration with a low approximate 2-5 watts of power required for the pump motor. This is an unexpected result when one compares it with the amount of energy required for a roller or centrifugal pump to pump dialysate or blood at similar flow rates through a dialyzer in a similar configuration. This is significant in that a small dual channel, battery operated and rechargeable wearable or portable dialysis device can be effectively manufactured and provide better performance than a large, heavy 120 volt AC powered set of roller or centrifugal pumps operating at similar flow rates.

A numerical simulation performed in addition to actual experimentation revealed that the enhanced transmembrane transport of an exemplary dual channel pulsatile pump configuration is primarily governed by diffusion across the fiber membranes, but the transmembrane transport is significantly increased over other pumping configurations due to the added convection created by the large, pulsed TMP across the membrane, which was produced by the counter-phased pulsatile pumping of the dialysate and blood circuits. Furthermore, it is believed that the enhanced clearances achieved by exemplary embodiments may be attributed to a washout or push-pull-like effect associated with the pulsatile flows through and along the fiber membrane boundaries. Referring back to FIG. 6B, it is shown that the flows of the dialysate and blood in the dialyzer are each similarly equally spaced pulses having flow rate maximums and minimums spaced substantially equally apart over predetermined periods of time. A predetermined period of time for the exemplary embodiments were about 2 pulses per second, but it is understood that the various embodiments of the invention may have a pulsatile pulsing flow rate of between about 0.5 and 4 pulses per second, with flow rates ranging from about 20-100 ml/min during steady state operation.

It will be appreciated by those skilled in the art having the benefit of this disclosure that this enhanced clearance in an artificial kidney incorporating a pulsatile pump provides an energy efficient device for performing dialysis. Such an exemplary device can be worn in-total on a patient as a completely wearable dialysis device or it may be incorporated into a portable device that may be carried or pushed (on a cart) by the patient or medical personnel. It should be understood that the drawings and detailed description herein are to be regarded in an illustrative rather than a restrictive manner, and are not intended to be limiting to the particular forms and examples disclosed. On the contrary, included are any further modifications, changes, rearrangements, substitutions, alternatives, design choices, and embodiments apparent to those of ordinary skill in the art, without departing from the spirit and scope hereof, as defined by the following claims. Thus, it is intended that the following claims be interpreted to embrace all such further modifications, changes, rearrangements, substitutions, alternatives, design choices, and embodiments.

What is claimed is:

1. A continuous renal replacement therapy (CRRT) device comprising:
   a blood pump channel for providing a pulsed blood flow, said pulsed blood flow being periodic such that each period comprises a high blood pressure portion having a first duration and a low blood pressure portion having a second duration, said first duration and said second duration having a duration ratio between about 3:4 and 4:3;
   a dialysate pump channel for providing a pulsed dialysate flow; said pulsed dialysate flow being periodic such that each period comprises a high dialysate pressure portion having said second duration and a low dialysate pressure portion having said first duration; wherein said high blood pressure portion and said low dialysate pressure portion occur, at least in part, during a first periodic time frame; and
   a dialyzer comprising:
   a blood inlet for receiving said pulsed blood flow;
   a plurality of fibers, each fiber comprising a semi permeable membrane exterior and a lumen extending the length of the fiber, said lumen being for said pulsed blood flow to flow through;
   a blood outlet for said pulsed blood flow to exit said dialyzer;
   a dialysate inlet for receiving said pulsed dialysate flow;
   a dialysate chamber, about said plurality of fibers, for said pulsed dialysate flow to flow through, and semi permeable membranes of said plurality of fibers being between each said lumen and said dialysate chamber; and
   a dialysate outlet for said pulsed dialysate flow to exit said dialyzer;
   wherein said blood pump channel, said dialysate channel and said dialyzer are configured to establish a peak Trans Membrane Pressure (TMP) across said semi permeable membranes of said plurality of fibers and between said pulsed blood flow in said lumens and said pulsed dialysate flow in said dialysate chamber, said peak TMP occurring during said first periodic time frame, said peak TMP being between about 70 mmHg and 120 mmHg.

2. The CRRT device of claim 1, wherein said low blood pressure portion and said high dialysate pressure portion both occur, at least in part, during a second periodic time frame, and wherein said blood pump channel, said dialysate channel and said dialyzer are configured to establish a minimum TMP across said semi permeable membranes of said plurality of fibers and between said pulsed blood flow in said lumens and said pulsed dialysate flow in said dialysate chamber, and wherein said minimum TMP occurs during said second periodic time frame, said minimum TMP being between about 10 mmHg and −10 mmHg.

3. The CRRT device of claim 1, wherein said CCRT device is completely wearable on a patient.

4. The CCRT device of claim 1, wherein said blood pump channel provides said pulsed blood flow with a periodic flow rate of between 0.5 and 4 Hz and wherein said dialysate pump channel provides a pulsed dialysate flow with said periodic flow rate.

5. The CRRT device of claim 2, wherein the combination of said peak TMP that occurs during said first periodic time frame and said minimum TMP that occurs during said second periodic time frame inhibit clogging of said lumens and semi permeable membranes.

6. The CRRT device of claim 1, wherein said pulsed blood flow is a pulsatile blood flow.

7. A continuous renal replacement therapy (CRRT) device comprising:
   a blood pump channel for providing a pulsatile blood flow, said pulsatile blood flow being periodic such that each period comprises a high blood pressure portion having a first duration and a low blood pressure portion having a second duration, said first duration and said second duration having a duration ratio of between about 3:4 and about 4:3;
   a dialysate pump channel for providing a pulsatile dialysate flow; said pulsatile dialysate flow being periodic such that each period comprises a high dialysate pressure portion having said second duration and a low dialysate pressure portion having said first duration; wherein said high blood pressure portion and said low dialysate pressure portion occur, at least in part, during a first periodic time frame; and
   a dialyzer comprising:
   a blood inlet for receiving said pulsatile blood flow;
   a plurality of fibers, each fiber comprising a semi permeable membrane exterior and a lumen extending the length of the fiber, said lumen being for said pulsatile blood flow to flow through;
   a blood outlet for said pulsatile blood flow to exit said dialyzer;
   a dialysate inlet for receiving said pulsatile dialysate flow;
   a dialysate compartment, about said plurality of fibers, for said pulsatile dialysate flow to flow through; and a dialysate outlet for said pulsatile dialysate flow to exit said dialyzer;

wherein said blood pump channel, said dialysate channel and said dialyzer are configured to establish a peak blood inlet-to-dialysate outlet differential pressure, said peak blood inlet-to-dialysate outlet differential pressure occurring during said first periodic time frame, said peak blood inlet-to-dialysate outlet differential pressure being between about 60 mmHg and about 150 mmHg.

8. The CRRT device of claim 7, wherein said low blood pressure portion and said high dialysate pressure portion both occur, at least in part, during a second periodic time frame, and wherein said blood pump channel, said dialysate channel and said dialyzer are configured to establish a minimum blood inlet-to-dialyzer output differential pressure, and wherein said minimum blood inlet-to-dialyzer output differential pressure occurs during said second periodic time frame, said minimum blood inlet-to-dialyzer output differential pressure being between about 10 mmHg and about −10 mmHg.

9. The CRRT device of claim 7, further comprising a dual channel pulsatile pump that comprises said blood pump channel and said dialysate pump channel.

10. The CRRT device of claim 7, wherein said CRRT device is completely wearable as a single device on a patient.

11. A method of continuous renal replacement therapy (CRRT) comprising:

pumping blood, by a pulsatile blood pump, to provide a pulsatile blood flow, said pulsatile blood flow being periodic such that each period comprises a high blood pressure portion having a first duration and low blood pressure portion having a second duration, said first duration and said second duration having a duration ratio of between about 3:4 and 4:3;

pumping dialysate, by a pulsatile dialysate pump, to provide a pulsatile dialysate flow, said pulsatile dialysate flow being periodic such that each period comprises a high dialysate pressure portion having said second duration and a low dialysate pressure portion having said first duration; wherein said high blood pressure portion and said low dialysate portion occur, at least in part, during a first periodic time frame;

establishing a blood inlet-to-dialysate outlet differential pressure between a blood inlet of a dialyzer and a dialysate outlet of said dialyzer; wherein said blood inlet-to-dialysate outlet differential pressure oscillates between a maximum differential pressure and a minimum differential pressure at a pump frequency of between 0.5 and 4 Hz;

wherein said maximum differential pressure has a range of between about 60 mmHg and about 150 mmHg.

12. The method of claim 11, wherein said minimum differential pressure has a range of between about 10 mmHg and about −10 mmHg for said pump frequency of between 0.5 and 4 Hz.

13. The method of claim 11, wherein said pulsatile blood pump and said pulsatile dialysate pump are each a separate pump channel of a dual channel pulsatile pump and are each operated by a same mechanical mechanism.

14. The method of claim 11, wherein pumping blood, by said pulsatile blood pump, further comprises pumping blood at an average pulsatile flow rate of between 30 and 90 milliliters/minute (ml/min).

15. The method of claim 11, wherein pumping dialysate, by said dialysate pump, further comprises pumping dialysate at an average pulsatile flow rate of between 30 and 90 ml/min.

* * * * *